(12) United States Patent
Farran et al.

(10) Patent No.: US 11,540,997 B2
(45) Date of Patent: Jan. 3, 2023

(54) SKIN PERFECTING COSMETIC COMPOSITIONS AND METHODS OF USE

(71) Applicant: L'OREAL, Paris (FR)

(72) Inventors: Alexandra Jane Elisa Farran, Dayton, NJ (US); Prabhjot K. Saini, Avenel, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 17/382,516

(22) Filed: Jul. 22, 2021

(65) Prior Publication Data

US 2022/0031602 A1 Feb. 3, 2022

Related U.S. Application Data

(60) Provisional application No. 63/059,460, filed on Jul. 31, 2020.

(30) Foreign Application Priority Data

Sep. 16, 2020 (FR) ........................................ 2009373

(51) Int. Cl.
| | | |
|---|---|---|
| A61K 8/25 | (2006.01) | |
| A61K 8/31 | (2006.01) | |
| A61K 8/81 | (2006.01) | |
| A61K 8/891 | (2006.01) | |
| A61Q 1/02 | (2006.01) | |
| A61Q 19/08 | (2006.01) | |
| A61K 8/86 | (2006.01) | |

(52) U.S. Cl.
CPC .............. *A61K 8/891* (2013.01); *A61K 8/25* (2013.01); *A61K 8/31* (2013.01); *A61K 8/8147* (2013.01); *A61K 8/86* (2013.01); *A61Q 1/02* (2013.01); *A61Q 19/08* (2013.01); *A61K 2800/43* (2013.01); *A61K 2800/48* (2013.01); *A61K 2800/524* (2013.01)

(58) Field of Classification Search
None
See application file for complete search history.

(56) References Cited

U.S. PATENT DOCUMENTS

| | | |
|---|---|---|
| 6,432,386 B1 | 8/2002 | Rollat-Corvol et al. |
| 8,691,202 B2 | 4/2014 | Yu et al. |
| 8,790,669 B2 | 7/2014 | Li et al. |
| 9,713,587 B2 | 7/2017 | Nijakowski |
| 9,814,669 B2 | 11/2017 | Shin et al. |
| 2005/0011018 A1 | 1/2005 | Greaves et al. |
| 2007/0140991 A1 | 6/2007 | Maitra et al. |
| 2007/0179241 A1 | 8/2007 | Patel |
| 2007/0224140 A1 | 9/2007 | Quadir et al. |
| 2011/0150802 A1 | 6/2011 | Bui et al. |
| 2011/0150806 A1 | 6/2011 | Bui et al. |
| 2011/0150807 A1 | 6/2011 | Bui et al. |
| 2012/0020907 A1 | 1/2012 | Bui et al. |
| 2013/0230477 A1 | 9/2013 | Li et al. |
| 2014/0286893 A1 | 9/2014 | Alden-Danforth et al. |
| 2015/0342845 A1 | 12/2015 | Hwang et al. |
| 2016/0175237 A1 | 6/2016 | Shin et al. |
| 2017/0035680 A1 | 2/2017 | Gosto et al. |
| 2017/0189299 A1 | 7/2017 | Manning et al. |
| 2017/0189320 A1 | 7/2017 | Chiou et al. |
| 2017/0334201 A1 | 11/2017 | Rijfers et al. |
| 2018/0015023 A1* | 1/2018 | Bernard ................. A61K 8/891 |
| 2019/0029930 A1 | 1/2019 | Deng et al. |
| 2020/0038311 A1* | 2/2020 | Noll ....................... A61K 8/416 |
| 2020/0276093 A1 | 9/2020 | Farran et al. |
| 2021/0196586 A1 | 7/2021 | Farran et al. |

FOREIGN PATENT DOCUMENTS

| | | |
|---|---|---|
| JP | 6101792 B2 | 3/2017 |
| WO | 2007078486 A2 | 7/2007 |
| WO | 2012030984 A2 | 3/2012 |
| WO | 2016100690 A1 | 6/2016 |

OTHER PUBLICATIONS

International Search Report and Written Opinion dated Nov. 15, 2021 for corresponding PCT Application No. PCT/US2021/042700.
SpecialChem. https://cosmetics.specialchem.com/inci/crotonic-acid-vinyl-c8-12-isoalkyl-esters-va-bis-vinyldimethicone-crosspolymer.
"SIMULGEL™ 600 Emulsifying-thickening polymer"; Oct. 2001.
"Tospearl 150 KA microspheres" Copyright 2003-2011.
Partial Search Report and Written Opinion dated Jun. 7, 2021 for corresponding French Application No. FR2009373.

* cited by examiner

*Primary Examiner* — Brian Gulledge
(74) *Attorney, Agent, or Firm* — Polsinelli PC

(57) ABSTRACT

Skin tightening compositions for application to the skin for providing an instantaneous and dramatic improvement to the appearance of skin. The skin tightening compositions typically include about 5 to about 45 wt. % or more of one or more hydrophobic film-forming polymers comprising acrylates/stearyl methacrylate copolymer; about 0.5 to about 20 wt. % of a mineral thickening agent; about 1 to about 15 wt. % of a silicone elastomer; and about 30 to about 85 wt. % of a volatile hydrocarbon oil, wherein all percentages by weight are based on the total weight of the skin tightening composition. Additionally, the skin tightening composition may have a weight ratio of the total amount of hydrophobic film-forming polymers to the total amount of mineral thickening agent is 1:1 to 10:1 and a weight ratio of the total amount of silicone elastomer to the total amount of mineral thickening agent is 1:2 to 8:1.

20 Claims, No Drawings

SKIN PERFECTING COSMETIC COMPOSITIONS AND METHODS OF USE

CROSS-REFERENCE TO RELATED APPLICATIONS

This application claims benefit of U.S. Provisional Application No. 63/059,460, filed Jul. 31, 2020, and French Patent Application No. 2009373, filed Sep. 16, 2020, which are incorporated herein by reference in their entirety.

FIELD OF THE DISCLOSURE

The present disclosure relates to skin tightening compositions for application to the skin for providing an instantaneous and dramatic improvement to the appearance of skin, for example, by reducing the appearance of wrinkles, eye bags, pores, and skin imperfections such as scarring, dark spots (and uneven skin tone), dark circles, and roughness.

BACKGROUND

Skin produces less collagen and elastin as it ages. For example, after the age of twenty, a person (human) produces about 1 percent less collagen in the skin each year. As a result, the skin becomes thinner and more fragile. Inevitably, wrinkles, crow's feet, age-spots, eye bags, and the like, begin to form.

Consumers often wish to improve the appearance of such age-related skin imperfections, preferably with instantaneous results. Many consumer products and procedures devoted to hiding and reducing wrinkles are available. Some products and procedures are simple and inexpensive, for example, applying make-up, particularly a primer or colored foundation, to cover the skin (and thereby cover and/or fill the wrinkles and provide a smoother look). Far more expensive and drastic procedures, such as surgical face lifts and Botox® injections, are also used to reduce the appearance of wrinkles. However, many consumers either cannot afford, or do not wish, to undergo such drastic cosmetic procedures. There are a number of lotions and creams that are formulated to hydrate the skin and make it more supple, thereby reducing the appearance of wrinkles. Some of these products contain active ingredients, for example, niacinamide, that help repair and rejuvenate skin over time. Unfortunately, however, all of these products and procedures have drawbacks.

Make-up products are often visible, offer minimal texture benefits, and have no long-term lasting effect on the skin. After removal of the make-up, the skin looks the same as before the make-up was applied. Common skin care products can have chronic, acute or both effects on the skin. Hydration and optical effects are common acute benefits, but these benefits quickly wear-off over time.

Attempts have been made to develop new categories of products to improve the appearance of skin without the drawbacks of existing products and procedures. One such family of products can be generally classified as "adhesive, contractile film-forming polymers." Film-forming polymers are chemical compositions that when applied to skin, leave a pliable, cohesive and continuous covering. A select group of film-forming polymers are also adhesive to the skin and contractile.

SUMMARY OF THE DISCLOSURE

The instant disclosure is directed to skin tightening compositions for providing an instantaneous and dramatic improvement to the appearance of skin, e.g., by reducing the appearance of wrinkles, eye bags, pores, and skin imperfections such as scarring, dark spots (and uneven skin tone), dark circles, and roughness.

The skin tightening compositions have a unique composition, which surprisingly have enhanced sebum resistance. In some instances, the skin tightening compositions provided improved long lasting wear. For example, some embodiments of the skin tightening composition may remain on a user's skin for up to about 5 hours, up to about 6 hours, up to about 7 hours, or up to about 8 hours without softening, being tacky/sticky, softening, loosing its tightening properties, cracking, peeling, and/or whitening. In some instances, the skin tightening compositions may have an enhanced odor profile. In addition to an enhanced odor profile, the skin tightening compositions may desirably exhibit excellent transparency, haze, and gloss characteristics after forming a film on a user's skin.

Skin tightening compositions according to an aspect of disclosure typically include:
- about 5 to about 45 wt. % or more of one or more hydrophobic film-forming polymers comprising acrylates/stearyl methacrylate copolymer;
- about 0.5 to about 20 wt. % of a mineral thickening agent, wherein a weight ratio of the total amount of hydrophobic film-forming polymers to the total amount of mineral thickening agent is 1:1 to 10:1;
- about 1 to about 15 wt. % of a silicone elastomer; and
- about 30 to about 85 wt. % of a volatile hydrocarbon oil, wherein a weight ratio of the total amount of silicone elastomer to the total amount of mineral thickening agent is 1:2 to 8:1, and all percentages by weight are based on the total weight of the skin tightening composition.

Non-limiting examples of suitable mineral thickening agents include silica silylate, fumed silica, zeolite, natural clay, synthetic clay, kaolin, hectorite, organically modified hectorite, pentaerythrityl tetraisostearate (and) disteardimonium hectorite (and) propylene carbonate, an activated clay, disteardimonium hectorite, stearalkonium hectorite, quaternium-18 bentonite, quaternium-18 hectorite, benzalkonium bentonite, or a mixture thereof.

The skin tightening composition may include a silicone elastomer that is chosen from non-emulsifying silicone elastomers, emulsifying silicone elastomers, and a mixture thereof. Preferably, the weight ratio of the total amount of silicone elastomer to the total amount of mineral thickening agent is 1:2 to 8:1, 1:1 to 5:1, or 1:1 to 4:1. Additionally, the weight ratio of the total amount of hydrophobic film-forming polymers to the total amount of mineral thickening agent is 1:1 to 10:1 or 1:1 to 7:1. In at least one instance, the skin tightening composition is anhydrous.

Additionally or alternatively, the skin tightening composition includes about 0.1 to about 20 wt. % of a non-volatile fatty compound, wherein the one or more non-volatile fatty compounds are chosen from polyolefins (petrolatum), waxes, squalane, squalene, hydrogenated polyisobutene, hydrogenated polydecene, polybutene, mineral oil, pentahydrosqualene, dimethicone, and a mixture thereof.

The skin tightening composition may include a volatile hydrocarbon that is chosen from isoparaffin, isohexadecane, isododecane, isodecane, undecane, tridecane, dodecane, isohexyl, isodecyl, neopentanoate, and a mixture thereof. Additionally or alternatively, the skin tightening composition may include about 1 to about 10 wt. % of a non-ionic surfactant. The skin tightening composition may comprise a non-ionic surfactant. Preferably, the non-ionic surfactant is chosen from dimethicone (and) peg/ppg-18/18 dimethicone, lauryl peg-9 polydimethylsiloxyethyl dimethicone, cetyl peg/ppg-10/1 dimethicone, peg-30 dipolyhydroxystearate, polyglyceryl-4 diisostearate/polyhydroxystearate/sebacate, polyglyceryl-4 isostearate, polyglyceryl-2 dipolyhydroxystearate, and a mixture thereof.

In some cases, the skin tightening composition may include about 1 to about 10 wt. % of a dispersant. The dispersant may be chosen from olyoxyethylene glycol ethers, POE/PEG ethers or esters, polyoxypropylene glycol ethers, PPG ethers or esters, sugar ethers or esters, glycerol or polyglycerol ethers or esters, and from ethoxylated glyceride esters, polyhydroxystearic acid, and a mixture thereof.

In some cases, the skin tightening compositions have about 0.01 to about 20 wt. % of an inorganic pigment, wherein the inorganic pigment is chosen from titanium dioxide, zirconium oxide, cerium oxide, zinc oxide, iron oxide, alumina, aluminum hydroxide, chromium oxide, manganese violet, ultramarine blue, chromium hydrate, ferric blue, aluminum powder, copper powder, silver powder, gold powder, barium sulfate, carbon black, mica, and a mixture thereof.

A soft powder in an amount of about 0.1 to about 20 wt. % may be included in the skin tightening composition. Suitable soft powders include talc, mica, titanated mica, alumina, aluminum silicate, silica which may or may not be coated, fumed silica, polyamide, methyl methacrylate crosspolymer, poly(methyl (meth)acrylate), polyethylene powder, polymethylsilsesquioxane powder, nylon-12, cellulose, nylon-12 fluorescent brightener salt (and) polyvinylalcohol crosspolymer, and a mixture thereof.

In accordance with another aspect of the disclosure, the skin tightening compositions may include:
  about 5 to about 45 wt. % of one or more hydrophobic film-forming polymers comprising acrylates/stearyl methacrylate copolymer;
  about 1 to about 35 wt. % of a thickening agent chosen from polyamide-8, hydrogenated styrene/isoprene copolymer, nylon-611/dimethicone copolymer, dimethicone/vinyl dimethicone crosspolymer, dimethicone crosspolymer, VP/EICOSENE copolymer, fumed silicas, hydrophobically modified silica, silica silylate, clays, and a combination thereof,
    wherein a weight ratio of the total amount of hydrophobic film-forming polymers to the total amount of thickening agent is 1:2 to 10:1;
  about 0.5 to about 20 wt. % of a filler; and
  about 20 to about 85 wt. % of a volatile hydrocarbon,
    wherein and all weight percentages are based on the total weight of the skin tightening composition.

The skin tightening compositions may be anhydrous. In some cases, the filler of the skin tightening composition is to be chosen from silica silylate, fumed silica, silica, nylon-12, cellulose, methyl methacrylate crosspolymer, silicone powder, and a mixture thereof. For instance, the filler may be silica silylate.

The skin tightening composition may include a volatile hydrocarbon that is chosen from isoparaffin, isohexadecane, isododecane, isodecane, undecane, tridecane, dodecane, isohexyl, isodecyl, neopentanoate, and a mixture thereof. Additionally or alternatively, the skin tightening composition may include about 1 to about 10 wt. % of a non-ionic surfactant. Preferably, the non-ionic surfactant is chosen from dimethicone (and) peg/ppg-18/18 dimethicone, lauryl peg-9 polydimethylsiloxyethyl dimethicone, cetyl peg/ppg-10/1 dimethicone, peg-30 dipolyhydroxystearate, polyglyceryl-4 diisostearate/polyhydroxystearate/sebacate, polyglyceryl-4 isostearate, polyglyceryl-2 dipolyhydroxystearate, and a mixture thereof.

In some cases, the skin tightening composition may include about 1 to about 10 wt. % of a dispersant. The dispersant may be chosen from olyoxyethylene glycol ethers, POE/PEG ethers or esters, polyoxypropylene glycol ethers, PPG ethers or esters, sugar ethers or esters, glycerol or polyglycerol ethers or esters, and from ethoxylated glyceride esters, polyhydroxystearic acid, and a mixture thereof.

An inorganic pigment may be included in the skin tightening composition. The inorganic pigment may be chosen from titanium dioxide, zirconium oxide, cerium oxide, zinc oxide, iron oxide, mica, alumina, aluminum hydroxide, chromium oxide, manganese violet, ultramarine blue, chromium hydrate, ferric blue, aluminum powder, copper powder, silver powder, gold powder, barium sulfate, carbon black, and a mixture thereof.

Methods for improving the appearance of skin according to yet a further aspect of the disclosure typically include the application of a skin tightening composition of the disclosure to skin. The method for improving the appearance of skin may comprise: reducing the appearance of fine lines of the skin;
  reducing the appearance of wrinkles of the skin;
  improving the tone of skin and/or improving the evenness of skin tone;
  improving skin softness and/or smoothness;
  reducing the appearance of eye bags;
  reducing the appearance of dark circles around and/or below the eyes;
  reducing the appearance of pores and/or scars; and/or
  increasing the radiance, luminosity, and/or glow of the skin.

DETAILED DESCRIPTION OF THE DISCLOSURE

The instant disclosure is directed to skin tightening compositions for providing an instantaneous and dramatic improvement to the appearance of skin, e.g., by reducing the appearance of wrinkles, eye bags, pores, and skin imperfections such as scarring, dark spots (and uneven skin tone), dark circles, and roughness. The inventors discovered that certain skin tightening compositions of the instant disclosure also exhibited excellent transparency, haze, and gloss characteristics after forming a film on a user's skin. Unlike other products, the films formed on the skin are particularly long lasting, and are not prone to dry-out, whitening, cracking, or peeling. Instead, they remain flexible (elastic), durable, and comfortable. Moreover, the compositions (and resulting films) hydrate and protect the underlying skin.

The skin tightening compositions may be formulated to have an enhanced sebum resistance. In some instances, the skin tightening compositions provided improved long lasting wear. For example, some embodiments of the skin tightening composition may remain on a user's skin for up to about 5 hours, up to about 6 hours, up to about 7 hours, or up to about 8 hours without softening, being tacky/sticky, losing its tightening properties, cracking, peeling, and/or whitening.

In some instances, skin tightening compositions have a unique composition, which have a surprising odor profile. While it was expected that certain ingredients would provide a chemical and/or resin odor, it was surprising that in certain embodiments of the disclosure that a natural odor profile was obtained. For example, certain embodiments of the disclosure provide a reduced resin smell, which is often associated with a chemical smell. In one instance, the skin tightening composition exhibits an enhanced natural smell and/or a reduced chemical smell Skin tightening compositions according to an aspect of disclosure typically include:
- about 5 to about 45 wt. % or more of one or more hydrophobic film-forming polymers comprising acrylates/stearyl methacrylate copolymer;
- about 0.5 to about 20 wt. % of a mineral thickening agent, wherein a weight ratio of the total amount of hydrophobic film-forming polymers to the total amount of mineral thickening agent is 1:1 to 10:1;
- about 1 to about 15 wt. % of a silicone elastomer; and
- about 30 to about 85 wt. % of a volatile hydrocarbon oil, wherein a weight ratio of the total amount of silicone elastomer to the total amount of mineral thickening agent is 1:2 to 8:1, and all percentages by weight are based on the total weight of the skin tightening composition.

The weight ratio of the total amount of hydrophobic film-forming polymers to the total amount of mineral thickening agent (film-forming polymers:mineral thickening agent) is 1:1 to 10:1. The ratio, however, may be greater than 1:1 (e.g., 1.1:1 or 1.2:1) to 10:1, i.e., the total amount of hydrophobic film-forming polymers is greater than the total amount of mineral thickening agent. In some instances, the ratio of the total amount of hydrophobic film-forming polymers to the total amount of mineral thickening agent (film-forming polymers:mineral thickening agent) is 1:1 to 8:11:1 to 7.5:1, 1:1 to 7:1, 1:1 to 6.5:1, 1:1 to 6:1, 1:1 to 5.5:1, 1:1 to 5:1, 1:1 to 4.5:1, 1:1 to 4:1, 1:1 to 3.5:1, 1:1 to 3:1, 1:1 to 2.5:1, 1:1 to 2:1, or any ranges and subranges thereof.

The weight ratio of the total amount of silicone elastomers to the total amount of mineral thickening agent (silicone elastomer:mineral thickening agent) is 1:2 to 8:1. The ratio, however, may be greater than 1:2 (e.g., 1.1:2 or 1.2:2) to 8:1, i.e., the total amount of silicone elastomers is greater than the total amount of mineral thickening agent. In some instances, the ratio of the total amount of silicone elastomers to the total amount of mineral thickening agent is 1:1 to 4:1, 1:1 to 3.5:1, 1:1 to 3:1, 1.1:1 to 4:1, 1.1 to 3.5:1, 1.1:1 to 3:1, 1.2:1 to 4:1, 1.2:1 to 3.5:1, or 1.2:1 to 3:1, or any ranges and subranges thereof.

In accordance with another aspect of the disclosure, the skin tightening compositions may include:
- about 5 to about 45 wt. % of one or more hydrophobic film-forming polymers comprising acrylates/stearyl methacrylate copolymer;
- about 1 to about 35 wt. % of a thickening agent chosen from polyamide-8, hydrogenated styrene/isoprene copolymer, nylon-611/dimethicone copolymer, dimethicone/vinyl dimethicone crosspolymer, dimethicone crosspolymer, VP/EICOSENE copolymer, fumed silicas, hydrophobically modified silica, silica silylate, clays, and a combination thereof, wherein a weight ratio of the total amount of hydrophobic film-forming polymers to the total amount of thickening agent is 1:2 to 10:1;
- about 0.5 to about 20 wt. % of a filler; and
- about 20 to about 85 wt. % of a volatile hydrocarbon, wherein and all weight percentages are based on the total weight of the skin tightening composition.

In some instances, the weight ratio of the at least one hydrophobic film-forming polymers to the at least one thickening agent is 1:2 to 8:1. Preferably, the weight ratio of the at least one hydrophobic film-forming polymers to the at least one thickening agent is 1:2 to 8:1, 1:1.5 to 8:1, 1:1 to 8:1, 1:2 to 7.5:1, 1:2 to 7:1, 1:2 to 6.5:1, 1:2 to 6:1, 1:2 to 5.5:1, 1:2 to 5:1, 1:2 to 4.5:1, 1:2 to 4:1, 1:2 to 3.5:1, 1:2 to 3:1, 1:2 to 2.5:1, 1:2 to 2:1, or any ranges and subranges thereof.

In addition, a unique and surprising aspect of the instant compositions is their ability to be formulated as aqueous compositions or as anhydrous (or essentially anhydrous) compositions. In some instances, the skin tightening compositions are anhydrous or essentially anhydrous (or substantially anhydrous). The term "essentially anhydrous" or "substantially anhydrous" means that the composition includes less than 5% by weight of water. Nonetheless, the composition may include less than about 4 wt. %, less than about 3 wt. %, less than about 2 wt. %, less than about 1 wt. %, less than about 0.5 wt. %, less than about 0.1 wt. % of water, less than about 0.05 wt. % water, or less than 0.01 wt. % water.

When the skin tightening compositions are aqueous compositions, the total amount of water in the skin tightening composition can vary but is typically 5 to about 40 wt. %, based on the total weight of the skin tightening composition. The total amount of water may be 5 to about 35 wt. %, 5 to about 30 wt. %, 5 to about 25 wt. %, 5 to about 20 wt. %, about 6 to about 40 wt. %, about 6 to about 35 wt. %, about 6 to about 30 wt. %, about 6 to about 25 wt. %, about 6 to about 20 wt. %, about 8 to about 40 wt. %, about 8 to about 35 wt. %, about 8 to about 30 wt. %, about 8 to about 25 wt. %, or about 8 to about 20 wt. %, based on the total weight of the skin tightening composition.

The skin tightening compositions may be in the form of a crème, a gel, a lotion, a serum, a paste, and the like. When the skin tightening compositions include water, they may be in the form of an emulsion, for example, a water-in-oil emulsion or an oil-in-water emulsion. In some instances, a water-in-oil emulsion is preferred.

The viscosity of the skin tightening compositions can vary. Nonetheless, in some instances, the viscosity is about 0.1 Pa·s to about 10,000 Pa·s at 25° C., and shear rate of 1 s$^{-1}$ at 25° C. The viscosity measurements can be carried out, for example, using a TA Instruments Rheometer, Model Discovery HR-3 (TA Instruments, New Castle Del.), with a 40 mm/2 degrees standard steel cone plate, and a flow procedure consisting of ramping the shear rate from 0.01 s$^{-1}$ to 1000 s$^{-1}$ at 25° C., following a conditioning step of 0.1 rad/sec for 30 sec at 25° C. In some instances, the viscosity is about 0.1 Pa·s to about 8,000 Pa·s, about 0.1 Pa·S to about 5,000 Pa·s, about 0.1 Pa·s to about 2,000 Pa·S, about 1 Pa·s to about 10,000 Pa·s, about 1 Pa·s to about 8,000 Pa·s, about 1 Pa·s to about 5,000 Pa·s, about 1 Pa·s to about 2,000 Pa·s, about 1 Pa·s to about 1,000 Pa·s, about 25 Pa·s to about 10,000 Pa·s, about 25 Pa·s to about 8,000 Pa·s, about 25 Pa·s to about 5,000 Pa·s, about 25 Pa·s to about 2,000 Pa·s, or about 25 Pa·s to about 1,000 Pa·s.

Suitable components, such as those listed below, may be included or excluded from the formulations for the skin-tightening compositions depending on the specific combination of other components, the form of the skin-tightening compositions, and/or the use of the formulation.

Film-Forming Polymer(s)

The skin tightening composition includes one or more film-forming polymers, comprising at least acrylates/stearyl methacrylate copolymer, typically in an amount of about 5 to about 45 wt. % wt. % or more, based on the total weight of the skin tightening composition. For example, the film-forming polymers may be present in the skin tightening composition in an amount of about 5 to about 45 wt. %, about 6 to about 45 wt. %, about 8 to about 45 wt. %, about 10 to about 45 wt. %, about 12 to about 45 wt. %; about 5 to about 45 wt. %; about 5 to about 40 wt. %, about 6 to about 40 wt. %, about 8 to about 40 wt. %, about 10 to about 40 wt. %, about 12 to about 40 wt. %; about 5 to about 35 wt. %, about 6 to about 35 wt. %, about 8 to about 35 wt. %, about 10 to about 35 wt. %, about 12 to about 35 wt. %; about 5 to about 35 wt. %; about 5 to about 30 wt. %, about 6 to about 30 wt. %, about 8 to about 30 wt. %, about 10 to about 30 wt. %, about 12 to about 30 wt. %; about 5 to about 25 wt. %, about 6 to about 25 wt. %, about 8 to about 25 wt. %, about 10 to about 25 wt. %, about 12 to about 25 wt. %; about 5 to about 20 wt. %, about 6 to about 20 wt. %, about 8 to about 20 wt. %, about 10 to about 20 wt. %, about 12 to about 20 wt. %; about 5 to about 18 wt. %, about 6 to about 18 wt. %, about 8 to about 18 wt. %, about 10 to about 18 wt. %, about 12 to about 18 wt. %; about 5 to about 16 wt. %, about 6 to about 16 wt. %, about 8 to about 16 wt. %, about 10 to about 16 wt. %, about 12 to about 16 wt. %, about 5 to about 14 wt. %, about 6 to about 14 wt. %, about 8 to about 14 wt. %, about 10 to about 14 wt. %, about 12 to about 14 wt. %, including all ranges and subranges thereof, based on the total weight of the skin tightening composition.

In some cases, the total amount of film-forming polymer is substantially acrylates/stearyl methacrylate copolymer. For instance, the film-forming polymer may consist essentially of or consist of acrylates/stearyl methacrylate copolymer. In other instances, the skin-tightening composition may include acrylates/stearyl methacrylate copolymer in any of the amounts listed above for the film-forming polymer(s).

The film-forming polymers may include one or more film-forming polymers in addition to the acrylates/stearyl methacrylate copolymer. The term "film-forming polymer" means a polymer that is capable of forming, by itself or in the presence of an auxiliary film-forming agent, a macroscopically continuous deposit on a support, especially on keratin materials, and preferably a cohesive deposit, and better still a deposit whose cohesion and mechanical properties are such that said deposit may be isolable and manipulate in isolation, for example when said deposit is prepared by pouring onto a non-stick surface, for instance a Teflon-coated or silicone-coated surface.

The term "hydrophobic film-forming polymer" denotes a film-forming polymer that has no or limited affinity for water and, in this respect, does not lend itself to a formulation in the form of a solute in an aqueous medium. In particular, the term "hydrophobic polymer" means a polymer having a solubility in water at 25° C. of less than 1% by weight.

The additional film-forming polymer may comprise or be chosen from any of the film-forming polymers described in PCT/EP2020/068143, which is incorporated herein in its entirety for all purposes.

As described in PCT/EP2020/068143, the additional film-forming polymer(s) may be in an oil dispersion comprising one or more particles of at least one polymer surface-stabilized with at least one stabilizer in a preferably anhydrous medium. For example, the aqueous dispersion may contain a hydrocarbon-based liquid fatty substance. The dispersions may consist of particles, which are generally spherical, and contain at least one surface-stabilized polymer, in an anhydrous medium. In some cases, the oily dispersion includes from 60% to 98% by weight, notably from 75% to 96% of monomers a) to c), as discussed below, relative to the total weight of polymers contained in said dispersion. The polymer particles i) of the dispersion (A) preferably have a number-mean size ranging from 5 to 500 nm, notably ranging from 10 to 400 nm and better still ranging from 20 to 300 nm. The final particle size is preferably greater than 100 nm. In particular, the number-mean size ranges from 100 nm to 500 nm, more particularly ranges from 150 nm to 400 nm and even more particularly ranges from 160 nm to 300 nm.

The film-forming polymer, or particles thereof, may be chosen from one or more of the following:
  a) ethylenic homopolymers of $(C_1-C_4)$alkyl $(C_1-C_{18})$(alkyl)acrylate, preferably $(C_1-C_{18})$alkyl (meth)acrylate ethylenic homopolymers;
  b) ethylenic copolymers of $(C_1-C_4)$alkyl $(C_1-C_{18})$(alkyl)acrylate, preferably $(C_1-C_{18})$alkyl (meth)acrylate, and of $(C_1-C_{18})$(alkyl)acrylic acid, preferably (meth)acrylic acid ethylenic copolymers; and
  c) ethylenic copolymers of $(C_1-C_4)$alkyl $(C_1-C_{18})$(alkyl)acrylate, preferably $(C_1-C_{18})$alkyl (meth)acrylate ethylenic copolymers.

In at least one preferred embodiment of the invention, the film-forming polymer is an ethylenic acrylate homopolymer resulting from the polymerization of an identical monomer having a structure according to the formula (I), below.

$$H_2C=C(R)-C(O)-O-R' \quad (I)$$

in which formula (I):
  R represents a hydrogen atom or a $(C_1-C_4)$alkyl group such as methyl, and
  R' represents a $(C_1-C_{18})$alkyl group such as methyl or ethyl, preferably monomer of formula (I) is a $C_1-C_{18}$ alkyl acrylate such as methyl acrylate.

According to another embodiment of the invention, the film-forming polymer may be ethylenic acrylate copolymer b) resulting from the polymerization:
  of at least one monomer of formula (I) as defined previously, preferably a $C_1-C_4$ alkyl acrylate such as methyl acrylate and ethyl acrylate; and
  of a monomer of formula (II), provided below.

$$H_2C=C(R)-C(O)-O-H \quad (II)$$

in which formula (II) R is as defined previously, in particular monomer of formula (II) is acrylic acid. The amount of acrylic acid ranges from 0.1% to 15% by weight relative to the weight of monomers of the particle i) and the polymer of the particles i) is in particular a copolymer derived from the copolymerization of acrylic acid with one or more $C_1-C_4$ alkyl (meth)acrylate monomers chosen in particular from methyl (meth)acrylate and ethyl (meth)acrylate.

According to another preferred embodiment of the invention, the polymer constituting the particles i) is an ethylenic acrylate copolymer b) derived from the polymerization:
  of at least two different monomers: of formula (I) as defined previously, preferably a $C_1-C_{18}$ alkyl acrylate such as methyl acrylate, ethyl acrylate and stearyl acrylate; and
  optionally of a monomer of formula (II) as defined previously.

According to a particular embodiment of the invention, the polymer of the particles i) is a polymer derived from $C_1-C_{18}$ alkyl (meth)acrylate monomers. The monomers are preferably chosen from methyl (meth)acrylate, ethyl (meth)acrylate, n-propyl (meth)acrylate, isopropyl (meth)acrylate, n-butyl (meth)acrylate and tert-butyl (meth)acrylate, stearyl (meth)acrylate and more preferentially chosen from methyl (meth)acrylate and stearyl (meth)acrylate.

Advantageously, a $C_1-C_4$ alkyl acrylate monomer is used. Preferentially, the monomers are chosen from methyl acrylate and ethyl acrylate. A $C_1-C_{18}$ alkyl methacrylate monomer is also particularly used. Preferentially, the monomers are chosen from methyl methacrylate, ethyl methacrylate and stearyl methacrylate, more particularly stearyl methacrylate.

In yet another example, the film-forming polymer includes from 2% to 40% by weight, in particular 4% to 25%, notably from 5% to 20% by weight of $(C_9\text{-}C_{22})$alkyl $(C_1\text{-}C_6)$(alkyl)acrylate monomers included in group d) or e) disclosed above, based on the total weight of film-forming polymers.

According to another instance, the particles i) include b) ethylenic copolymers of b1) $(C_1\text{-}C_4)$alkyl $(C_1\text{-}C_{18})$(alkyl)acrylate and of b2) ethylenic monomers comprising one or more carboxyl, anhydride, phosphoric acid, sulfonic acid and/or aryl groups such as benzyl. The ethylenic monomers may comprise one or more carboxyl, anhydride, phosphoric acid, sulfonic acid, and/or aryl groups chosen from (1), (2), (3), (4) and (5), which are described below:

(1) $R^1(R^2)C=C(R^3)$-Acid with $R^1$, $R^2$ and $R^3$ representing a hydrogen atom or a $CO_2H$, $H_2PO_4$ or $SO_3H$ group, and Acid representing a carboxyl, phosphoric acid or sulfonic acid, preferably carboxyl, it being understood that $R^1$, $R^2$ and $R^3$ cannot simultaneously represent a hydrogen atom;

(2) $H_2C=C(R)-C(O)-N(R')$-Alk-Acid with R and R', which may be identical or different, representing a hydrogen atom or a $(C_1\text{-}C_4)$alkyl group; Alk represents a $(C_1\text{-}C_6)$alkylene group optionally substituted with at least one group chosen from Acid as defined previously and hydroxyl; and Acid is as defined previously, preferably carboxyl or sulfonic acid;

(3) $Ar-(R^a)C=C(R^b)-R^c$ with $R^a$, $R^b$ and $R^c$, which may be identical or different, representing a hydrogen atom or a $(C_1\text{-}C_4)$alkyl group, and Ar representing an aryl group, preferably benzyl, optionally substituted with at least one acid group $CO_2H$, $H_2PO_4$, or $SO_3H$, preferably substituted with a $CO_2H$ or $SO_3H$ group, (4) maleic anhydride of formulae (4a) and (4b):

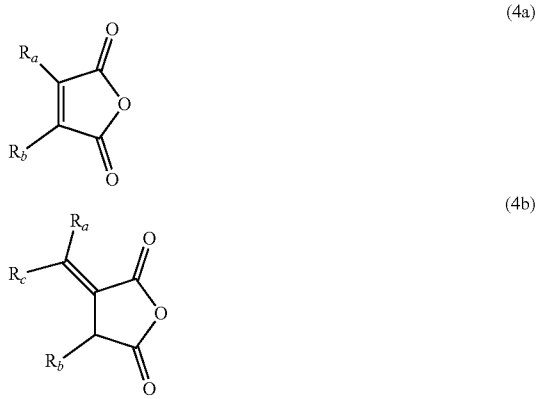

(4a)

(4b)

in which formulae (4a) and (4b) $R_a$, $R_b$ and $R_c$, which may be identical or different, represent a hydrogen atom or a $(C_1\text{-}C_4)$alkyl group; preferably, $R_a$, $R_b$, and $R_c$ represent a hydrogen atom. Preferentially, the ethylenically unsaturated anhydride monomer of the invention is of formula (4b) and more preferentially is maleic anhydride; and (5) $H_2C=C(R)-C(O)-O-H$ with R representing a hydrogen atom or a $(C_1\text{-}C_4)$alkyl group such as methyl.

Preferably, b2) is a $(C_1\text{-}C_4)$(alkyl)acrylic acid, e.g., b) may be copolymers of $(C_1\text{-}C_4)$alkyl (meth)acrylate and of (meth)acrylic acid. In one instance, b2) is chosen from crotonic acid, maleic acid, itaconic acid, fumaric acid, styrenesulfonic acid, vinylbenzoic acid, vinylphosphoric acid, acrylic acid, methacrylic acid, acrylamidopropanesulfonic acid, acrylamidoglycolic acid, and salts thereof; preferably, b2) represents acrylic acid.

The film-forming polymers, or particles thereof, may be in a dispersion with stabilizers, such as ethylenic homopolymers of $(C_9\text{-}C_{22})$alkyl $(C_1\text{-}C_6)$(alkyl)acrylate, in particular ethylenic homopolymers of $(C_9\text{-}C_{18})$alkyl $(C_1\text{-}C_4)$(alkyl)acrylate, preferably ethylenic homopolymers of $(C_9\text{-}C_{22})$alkyl (meth)acrylate and more preferentially ethylenic homopolymers of $(C_9\text{-}C_{18})$alkyl (meth)acrylate. The $(C_9\text{-}C_{22})$alkyl or the $(C_9\text{-}C_{18})$alkyl groups may be linear or branched. In at least one case, the stabilizer(s) ii) consist of ethylenic polymers chosen from d) ethylenic homopolymers resulting from the polymerization of monomers of formula $H_2C=C(R)-C(O)-O-R''$ with R representing a hydrogen atom or a $(C_1\text{-}C_4)$alkyl group such as methyl, and R" representing a $(C_9\text{-}C_{22})$alkyl and preferably $(C_9\text{-}C_{18})$alkyl group. R" may represent isodecyl, lauryl, stearyl, hexadecyl or behenyl. R" may, alternatively represent a linear $(C_9\text{-}C_{22})$alkyl and, preferably, a linear $(C_9\text{-}C_{18})$alkyl group. According to another particular embodiment of the invention, the stabilizer(s) ii) are chosen from e) ethylenic copolymers of $(C_9\text{-}C_{22})$alkyl $(C_1\text{-}C_6)$(alkyl)acrylate and of $(C_1\text{-}C_4)$alkyl $(C_1\text{-}C_4)$(alkyl)acrylate, particularly copolymers of $(C_9\text{-}C_{18})$alkyl $(C_1\text{-}C_4)$(alkyl)acrylate and of $(C_1\text{-}C_4)$alkyl $(C_1\text{-}C_4)$(alkyl)acrylate, preferably copolymers of $(C_9\text{-}C_{18})$alkyl (meth)acrylate and of $(C_1\text{-}C_4)$alkyl (meth)acrylate.

The stabilizer(s) ii) may chosen from the ethylenic copolymers e) of formulae (III) and (IV):

$$H_2C=C(R)-C(O)-O-R' \quad \text{(III)}$$

$$H_2C=C(R)-C(O)-O-R'' \quad \text{(IV)}$$

in which formulae (III) and (IV):
R, which may be identical or different, represent a hydrogen atom or a $(C_1\text{-}C_4)$alkyl group such as methyl,
R', which may be identical or different, represent a $(C_1\text{-}C_4)$alkyl group such as methyl or ethyl, and
R" represents a $(C_9\text{-}C_{22})$alkyl, preferably $(C_{10}\text{-}C_{20})$alkyl and in particular $(C_{2n})$alkyl group with n being an integer equal to 5, 6, 7, 8, 9 or 10. Preferably, R" represents isodecyl, lauryl, stearyl, hexadecyl or behenyl.

Preferentially, the stabilizer(s) ii) are chosen from copolymers derived from monomers chosen from isodecyl, lauryl, stearyl, hexadecyl and behenyl (meth)acrylates and $C_1\text{-}C_4$ alkyl (meth)acrylate, preferably methyl (meth)acrylate. More preferentially, the stabilizer(s) ii) are chosen from copolymers derived from monomers chosen from isodecyl, lauryl, stearyl and hexadecyl (meth)acrylates and $C_1\text{-}C_4$ alkyl (meth)acrylate, preferably methyl (meth)acrylate or ethyl (meth)acrylate. In particular, the stabilizer ii) may be chosen from isodecyl, lauryl, stearyl, hexadecyl or behenyl (meth)acrylate homopolymer and statistical copolymers of isodecyl, lauryl, stearyl, hexadecyl or behenyl (meth)acrylate and of $C_1\text{-}C_4$ alkyl (meth)acrylate preferably present in a lauryl, stearyl, hexadecyl or behenyl (meth)acrylate/$C_1\text{-}C_4$ alkyl (meth)acrylate weight ratio of greater than 4.5. Said weight ratio may range from 5 to 15 and preferably from 5.5 to 12.

According to another instance, the stabilizer(s) ii) are chosen from ethylenic copolymers e) derived from the polymerization of a monomer of formula (IV) as described above and two different monomers of formula (III), as described above. In one instance, the stabilizer(s) ii) are chosen from copolymers derived from the polymerization of one monomer chosen from isodecyl, lauryl, stearyl, hexadecyl and behenyl (meth)acrylates and of two different $C_1$-$C_4$ alkyl (meth)acrylates, preferably methyl acrylate and ethyl acrylate. In particular, the weight ratio of isodecyl, lauryl, stearyl, hexadecyl or behenyl (meth)acrylates/$C_1$-$C_4$ alkyl (meth)acrylate is greater than 4. Advantageously, said weight ratio ranges from 5 to 15 and more preferentially said weight ratio ranges from 5.5 to 11. In at least one other instance, the stabilizer(s) ii) are chosen from ethylenic copolymers e) derived from the polymerization of a monomer of formula (III) as defined in the preceding claim and two different monomers of formula (IV) as defined previously. For example, the stabilizer(s) ii) may be chosen from copolymers derived from the polymerization of two different monomers chosen from isodecyl, lauryl, stearyl, hexadecyl and behenyl (meth)acrylates and of one $C_1$-$C_4$ alkyl (meth)acrylate monomer, preferably methyl acrylate and ethyl acrylate; in particular, the weight ratio of isodecyl, lauryl, stearyl, hexadecyl or behenyl (meth)acrylates/$C_1$-$C_4$ alkyl (meth)acrylate is greater than 4. Said weight ratio may range from 4.5 to 10 or from 5 to 8.

In one case, the stabilizer(s) ii) are chosen from copolymers derived from the polymerization of two different monomers chosen from isodecyl, lauryl, stearyl, hexadecyl and behenyl (meth)acrylates and of one $C_1$-$C_4$ alkyl (meth)acrylate monomer, preferably methyl acrylate and ethyl acrylate; in particular, the weight ratio of isodecyl, lauryl, stearyl, hexadecyl or behenyl (meth)acrylates/$C_1$-$C_4$ alkyl (meth)acrylate in the dispersion (A) is less than 1. Particularly, said weight ratio may range from 0.05 to 0.5 and more preferentially said weight ratio ranges from 0.08 to 0.2 in the dispersion (A). According to a particular example, the stabilizer(s) ii) may be present in a content ranging from 2% to 40% by weight, notably from 3% to 30% by weight and preferably from 4% to 25% by weight relative to the weight of polymer(s) present in the dispersion (A). Preferably, the stabilizer(s) ii) and the particle(s) i) have a number-average molecular weight (Mn) of between 1000 and 1000000 g/mol, notably between 5000 and 500000 g/mol and even better still between 10000 and 300000 g/mol.

Additionally or alternatively, the film-forming polymer(s) may be chosen from acrylic acid/isobutyl acrylates/isobornyl acrylate copolymer, trimethylsiloxysilicate, acrylates/isobornyl acrylate copolymer, norbornene/tris(trimethylsiloxy)silylnorbornene copolymer, acrylate/polytrimethyl siloxymethacrylate copolymer, acrylates/polymethylsiloxymethacrylate copolymer, $C_{30-45}$ alkyldimethylsilylpolypropylsilsequixane, trimethylsilsesquixane, polypropylsilsesquixane, acrylates/dimethicone copolymer, octylacrylamide/acrylates/butylaminoethyl methacrylate copolymer, VA/butyl maleate/isobornyl acrylate copolymer, acrylates/t-butylacrylamide copolymer, polyvinylpyrrolidone/vinyl acetate copolymer, triacontanyl PVP copolymer, acrylates/dimethylaminoethyl methacrylate copolymer, and a combination thereof. In some cases, the at least one film-forming polymers includes one or more of acrylic acid/isobutyl acrylates/isobornyl acrylate copolymer, trimethylsiloxysilicate, acrylates/isobornyl acrylate copolymer, norbornene/tris(trimethylsiloxy)silylnorbornene copolymer, acrylates/polymethylsiloxymethacrylate copolymer, and a combination thereof.

The film-forming polymers may be a hydrophobic film-forming polymer. The term "hydrophobic film-forming polymer" denotes a film-forming polymer that has no or limited affinity for water and, in this respect, does not lend itself to a formulation in the form of a solute in an aqueous medium. In particular, the term "hydrophobic polymer" means a polymer having a solubility in water at 25° C. of less than 1% by weight.

The film-forming polymers may be chosen from the following and, optionally hydrophobic:
film-forming polymers that are soluble in an organic solvent medium, in particular liposoluble polymers; this means that the polymer is soluble or miscible in the organic medium and forms a single homogeneous phase when it is incorporated into the medium; and
film-forming polymers that are dispersible in an organic solvent medium, which means that the polymer forms an insoluble phase in the organic medium, the polymer remaining stable and/or compatible once incorporated into this medium. In particular, such polymers may be in the form of non-aqueous dispersions of polymer particles, preferably dispersions in silicone oils or hydrocarbon-based oils; in one embodiment, the non-aqueous polymer dispersions comprise polymer particles stabilized on their surface with at least one stabilizer; these non-aqueous dispersions are often referred to as NADs.

Hydrophobic film-forming polymers that may be mentioned include homopolymers and copolymers of a compound bearing an ethylenic unit, acrylic polymers and copolymers, polyurethanes, polyesters, silicone polymers such as polymers bearing a non-silicone organic backbone grafted with monomers containing a polysiloxane, and polyisoprenes.

In some instances, useful hydrophobic film-forming polymers include lipodispersible film-forming polymers in the form of non-aqueous dispersions of polymer particles, block ethylenic copolymers, vinyl polymers comprising at least one carbosiloxane dendrimer-based unit, silicone acrylate copolymers and mixtures thereof, preferably lipodispersible film-forming polymers in the form of non-aqueous dispersions of polymer particles (NADs).

Lipodispersible Film-Forming Polymers in the Form of Non-Aqueous Dispersions of Polymer Particles, Also Known as NADs Non-aqueous dispersions of hydrophobic film-forming polymer that may be used include dispersions of particles of a grafted ethylenic polymer, preferably an acrylic polymer, in a liquid oily phase for example, in the form of surface-stabilized particles dispersed in the liquid fatty phase. The dispersion of surface-stabilized polymer particles may be manufactured as described in document WO 04/055081, which is incorporated herein by reference in its entirety.

Block Ethylenic Copolymer

The film-forming polymers may be a block ethylenic copolymer, containing at least a first block with a glass transition temperature ($T_g$) of greater than or equal to 40° C. and being totally or partly derived from one or more first monomers, which are such that the homopolymer prepared from these monomers has a glass transition temperature of greater than or equal to 40° C., and at least a second block with a glass transition temperature of less than or equal to 20° C. and being derived totally or partly from one or more second monomers, which are such that the homopolymer prepared from these monomers has a glass transition temperature of less than or equal to 20° C., said first block and said second block being connected together via a statistical intermediate segment comprising at least one of said first constituent monomers of the first block and at least one of said second constituent monomers of the second block, and said block copolymer having a polydispersity index I of greater than 2. Polymers of this type that are suitable for use in the invention are described in document EP 1 411 069, which is incorporated herein by reference in its entirety. A non-limiting examples includes the product MEXOMER PAS (acrylic acid/isobutyl acrylate/isobornyl acrylate copolymer diluted to 50% in isododecane) sold by the company Chimex.

Vinyl Polymer Comprising at Least One Carbosiloxane Dendrimer-Based Unit

The hydrophobic film-forming polymer may be at least one vinyl polymer comprising at least one carbosiloxane dendrimer-based unit. The vinyl polymer typically has a backbone and at least one side chain, which comprises a carbosiloxane dendrimer-based unit having a carbosiloxane dendrimer structure. Vinyl polymers comprising at least one carbosiloxane dendrimer unit as described in applications WO 03/045337 and EP 963751, which are incorporated herein by reference in their entirety.

The term "carbosiloxane dendrimer structure" is a molecular structure with branched groups of high molecular masses, said structure having high regularity in the radial direction starting from the bond to the backbone. Such carbosiloxane dendrimer structures are described in the form of a highly branched siloxane-silylalkylene copolymer in the laid-open Japanese patent application Kokai 9-171154, which is incorporated herein by reference in their entirety.

A vinyl polymer bearing at least one carbosiloxane dendrimer-based unit has a molecular side chain containing a carbosiloxane dendrimer structure, and may be derived from the polymerization of:

(A) from 0 to 99.9 parts by weight of a vinyl monomer; and (B) from 100 to 0.1 part by weight of a carbosiloxane dendrimer containing a radical-polymerizable organic group, represented by the general formula:

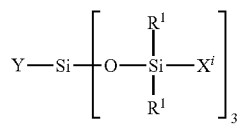

in which Y represents a radical-polymerizable organic group, $R^1$ represents an aryl group or an alkyl group containing from 1 to 10 carbon atoms, and $X^1$ represents a silylalkyl group which, when i=1, is represented by the formula:

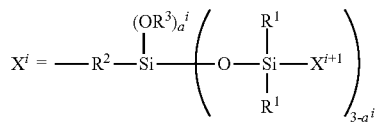

in which $R^1$ is as defined above, $R^2$ represents an alkylene group containing from 2 to 10 carbon atoms, $R^3$ represents an alkyl group containing from 1 to 10 carbon atoms, $X^{i+1}$ represents a hydrogen atom, an alkyl group containing from 1 to 10 carbon atoms, an aryl group, or the silylalkyl group defined above with i=i+1; i is an integer from 1 to 10 which represents the generation of said silylalkyl group, and a' is an integer from 0 to 3;

in which said radical-polymerizable organic group contained in the component (A) is chosen from:

organic groups containing a methacrylic group or an acrylic group and that are represented by the formulae:

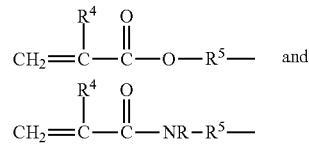

in which $R^4$ represents a hydrogen atom or an alkyl group, $R^5$ represents an alkylene group containing from 1 to 10 carbon atoms; and organic groups containing a styryl group and that are represented by the formula:

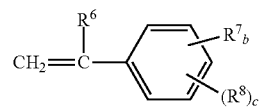

in which $R^6$ represents a hydrogen atom or an alkyl group, $R^7$ represents an alkyl group containing from 1 to 10 carbon atoms, $R^8$ represents an alkylene group containing from 1 to 10 carbon atoms, b is an integer from 0 to 4, and c is 0 or 1, such that if c is 0, $-(R^8)_c-$ represents a bond.

The monomer of vinyl type that is the component (A) in the vinyl polymer is a monomer of vinyl type that contains a radical-polymerizable vinyl group.

The following are examples of this monomer of vinyl type: methyl methacrylate, ethyl methacrylate, n-propyl methacrylate, isopropyl methacrylate or a methacrylate of an analogous lower alkyl; glycidyl methacrylate; butyl methacrylate, butyl acrylate, n-butyl methacrylate, isobutyl methacrylate, tert-butyl acrylate, tert-butyl methacrylate, n-hexyl methacrylate, cyclohexyl methacrylate, 2-ethylhexyl acrylate, 2-ethylhexyl methacrylate, octyl methacrylate, lauryl methacrylate, stearyl acrylate, stearyl methacrylate or a higher-analogue methacrylate; vinyl acetate, vinyl propionate or a vinyl ester of an analogous lower fatty acid; vinyl caproate, vinyl 2-ethylhexoate, vinyl laurate, vinyl stearate or an ester of an analogous higher fatty acid; styrene, vinyltoluene, benzyl methacrylate, phenoxyethyl methacrylate, vinylpyrrolidone or similar vinylaromatic monomers; methacrylamide, N-methylolmethacrylamide, N-methoxymethyl-methacrylamide, isobutoxymethoxymethacrylamide, N,N-dimethylmethacrylamide or similar monomers of vinyl type containing amide groups; hydroxyethyl methacrylate, hydroxypropyl alcohol methacrylate or similar monomers of vinyl type containing hydroxyl groups; acrylic acid, methacrylic acid, itaconic acid, crotonic acid, fumaric acid, maleic acid or similar monomers of vinyl type containing a carboxylic acid group; tetrahydrofurfuryl methacrylate, butoxyethyl methacrylate, ethoxydiethylene glycol methacrylate, polyethylene glycol methacrylate, polypropylene glycol monomethacrylate, hydroxybutyl vinyl ether, cetyl vinyl ether, 2-ethylhexyl vinyl ether or a similar monomer of vinyl type with ether bonds; methacryloxypropyltrimethoxysilane, polydimethylsiloxane containing a methacrylic group on one of its molecular ends, polydimethylsiloxane containing a styryl group on one of its molecular ends, or a similar silicone compound containing unsaturated groups; butadiene; vinyl chloride; vinylidene chloride;

methacrylonitrile; dibutyl fumarate; anhydrous maleic acid; anhydrous succinic acid; methacryl glycidyl ether; an organic salt of an amine, an ammonium salt, and an alkali metal salt of methacrylic acid, of itaconic acid, of crotonic acid, of maleic acid or of fumaric acid; a radical-polymerizable unsaturated monomer containing a sulfonic acid group such as a styrenesulfonic acid group; a quaternary ammonium salt derived from methacrylic acid, such as 2-hydroxy-3-methacryloxypropyltrimethylammonium chloride; and a methacrylic acid ester of an alcohol containing a tertiary amine group, such as a methacrylic acid ester of diethylamine.

Multifunctional monomers of vinyl type may, optionally, be included in certain cases. The following are examples of such compounds: trimethylolpropane trimethacrylate, pentaerythrityl trimethacrylate, ethylene glycol dimethacrylate, tetraethylene glycol dimethacrylate, polyethylene glycol dimethacrylate, 1,4-butanediol dimethacrylate, 1,6-hexanediol dimethacrylate, neopentyl glycol dimethacrylate, trimethylolpropane trioxyethylmethacrylate, tris(2-hydroxyethyl) isocyanurate dimethacrylate, tris(2-hydroxyethyl) isocyanurate trimethacrylate, polydimethylsiloxane capped with styryl groups bearing divinylbenzene groups on the two ends, or similar silicone compounds bearing unsaturated groups.

To facilitate the preparation of starting material mixture for cosmetic products, the number-average molecular mass of the vinyl polymer bearing a carbosiloxane dendrimer may be chosen within the range between 3,000 g/mol and 2,000,000 g/mol and preferably between 5,000 g/mol and 800,000 g/mol. It may be a liquid, a gum, a paste, a solid, a powder, or any other form. The preferred forms are solutions consisting of the dilution of a dispersion or of a powder in solvents such as a silicone oil or an organic oil.

According to one embodiment, a vinyl polymer grafted in the sense of the present disclosure may be conveyed in an oil or a mixture of oils, which is/are preferably volatile, chosen in particular from silicone oils and hydrocarbon-based oils, and mixtures thereof. A non-limiting silicone oil that may, optionally be used is cyclopentasiloxane. Similarly, a non-limiting hydrocarbon-based oil that is may be used is isododecane.

Vinyl polymers grafted with at least one carbosiloxane dendrimer-based unit include the polymers sold under the names TIB 4-100, TIB 4-101, TIB 4-120, TIB 4-130, TIB 4-200, FA 4002 ID (TIB 4-202), TIB 4-220 and FA 4001 CM (TIB 4-230) by the company Dow Corning.

In some instances, the vinyl polymer grafted with at least one carbosiloxane dendrimer-based unit is an acrylate/polytrimethyl siloxymethacrylate copolymer, for example, the product sold in isododecane under the name Dow Corning FA 4002 ID Silicone Acrylate.

Silicone Acrylate Copolymers

In some instances, one or more of the film-forming polymers include at least one copolymer comprising carboxylate groups and polydimethylsiloxane groups. The term "copolymer comprising carboxylate groups and polydimethylsiloxane groups" means a copolymer obtained from (a) one or more carboxylic (acid or ester) monomers, and (b) one or more polydimethylsiloxane (PDMS) chains. The term "carboxylic monomer" means both carboxylic acid monomers and carboxylic acid ester monomers.

The monomer (a) may be chosen, for example, from acrylic acid, methacrylic acid, maleic acid, fumaric acid, itaconic acid, crotonic acid, esters thereof and mixtures of these monomers. Esters that may be mentioned include the following monomers: acrylate, methacrylate, maleate, fumarate, itaconate and/or crotonate. According to at least one embodiment of the invention, the monomers in ester form are more particularly chosen from linear or branched, preferably $C_1$-$C_{24}$ and better still $C_1$-$C_{22}$ alkyl acrylates and methacrylates, the alkyl radical preferably being chosen from methyl, ethyl, stearyl, butyl and 2-ethylhexyl radicals, and mixtures thereof. Thus, in some instances, the copolymer comprises as carboxylate groups at least one group chosen from acrylic acid and methacrylic acid, and methyl, ethyl, stearyl, butyl or 2-ethylhexyl acrylate or methacrylate, and mixtures thereof.

The term "polydimethylsiloxanes" (also known as organopolysiloxanes and abbreviated as PDMS) denotes any organosilicon polymer or oligomer of linear structure, of variable molecular weight, obtained by polymerization and/or polycondensation of suitably functionalized silanes, and consisting essentially of a repetition of main units in which the silicon atoms are linked together via oxygen atoms (siloxane bond ≡Si—O—Si≡), comprising trimethyl radicals directly linked via a carbon atom to said silicon atoms. The PDMS chains that may be used to obtain the copolymer may comprise at least one polymerizable radical group, preferably located on at least one of the ends of the chain, i.e. the PDMS may contain, for example, a polymerizable radical group on the two ends of the chain or one polymerizable radical group on one end of the chain and one trimethylsilyl end group on the other end of the chain. The polymerizable radical group may especially be an acrylic or methacrylic group, in particular a group $CH_2$=$CR_1$—CO—O—$R_2$, in which $R_1$ represents a hydrogen or a methyl group and $R_2$ represents —$CH_2$—, —$(CH_2)_n$— with n=3, 5, 8 or 10, —$CH_2$—$CH(CH_3)$—$CH_2$—, —$CH_2$—$CH_2$—O—$CH_2$—$CH_2$—, —$CH_2$—$CH_2$—O—$CH_2$—$CH_2$—$CH(CH_3)$—$CH_2$—, —$CH_2$—$CH._2$—O—$CH_2$—, or —$CH_2$—O—$CH_2$—$CH_2$—$CH_2$—.

The copolymers are generally obtained according to the usual methods of polymerization and grafting, for example by free-radical polymerization (A) of a PDMS comprising at least one polymerizable radical group (for example on one of the ends of the chain or on both ends) and (B) of at least one carboxylic monomer. The copolymers obtained may have a molecular weight ranging from about 3,000 g/mol to 200,000 g/mol and preferably from about 5,000 g/mol to 100,000 g/mol. The copolymer may be in its native form or in dispersed form in a solvent such as lower alcohols containing from 2 to 8 carbon atoms, for instance isopropyl alcohol, or oils, for instance volatile silicone oils (for example, cyclopentasiloxane).

Additional copolymers that mention may be made include copolymers of acrylic acid and of stearyl acrylate containing polydimethylsiloxane grafts, copolymers of stearyl methacrylate containing polydimethylsiloxane grafts, copolymers of acrylic acid and of stearyl methacrylate containing polydimethylsiloxane grafts, copolymers of methyl methacrylate, butyl methacrylate, 2-ethylhexyl acrylate and stearyl methacrylate containing polydimethylsiloxane grafts. Mention may also be made in particular of the copolymers sold by the company Shin-Etsu under the names KP-561 (CTFA name: acrylates/dimethicone), KP-541 in which the copolymer is dispersed at 60% by weight in isopropyl alcohol (CTFA name: acrylates/dimethicone and isopropyl alcohol), and KP-545 in which the copolymer is dispersed at 30% in cyclopentasiloxane (CTFA name: acrylates/dimethicone and cyclopentasiloxane). Mention may also be made of the grafted copolymer of polyacrylic acid and dimethylpolysiloxane dissolved in isododecane, sold by the company Shin-Etsu under the name KP-550.

Adhesive Polymer

The skin tightening composition may include one or more film-forming polymers that are adhesive polymers. In various embodiments, the at least one adhesive polymer may be amorphous, crystalline, or semicrystalline. In some instances, the adhesive polymer may have a $T_g$ greater than about 25° C., such as greater than about 50° C., greater than about 75° C., or greater than about 100° C., according to various embodiments. In further instances, the adhesive polymer may have a $T_g$ less than about 25° C., such as less than about 0° C., less than about −25° C., or less than about −50° C.

As non-limiting examples of adhesive polymers having a $T_g$ greater than about 25° C. may be mentioned polymer particles of $C_1$-$C_4$ alkyl(methacrylate)polymer, stabilized in a non-aqueous dispersion, referred to herein for ease of reference as an "oil dispersion," such as those described in WO2015/091513 which is incorporated by reference herein. By way of example, the $C_1$-$C_4$ alkyl (meth)acrylate monomers may be chosen from methyl (meth)acrylate, ethyl (meth)acrylate, n-propyl (meth)acrylate, isopropyl (meth)acrylate, n-butyl (meth)acrylate and tert-butyl (meth)acrylate. For example, the polymer may be a methyl acrylate and/or ethyl acrylate polymer.

The polymer may also comprise an ethylenically unsaturated acid monomer or the anhydride thereof, chosen especially from ethylenically unsaturated acid monomers comprising at least one carboxylic, phosphoric or sulfonic acid function, such as crotonic acid, itaconic acid, fumaric acid, maleic acid, maleic anhydride, styrenesulfonic acid, vinylbenzoic acid, vinylphosphoric acid, acrylic acid, methacrylic acid, acrylamidopropanesulfonic acid or acrylamidoglycolic acid, and salts thereof. For example, the ethylenically unsaturated acid monomer may be chosen from (meth)acrylic acid, maleic acid, and maleic anhydride.

Thickening Agent(s)

The skin tightening composition includes at least one thickening agent. According to at least one aspect of the disclosure, the thickening agent is a mineral thickening agent. In accordance with another aspect of the disclosure, the thickening agent(s) may include or be chosen from polyamide-8, hydrogenated styrene/isoprene copolymer, nylon-611/dimethicone cropolymer, dimethicone/vinyl dimethicone crosspolymer, dimethicone crosspolymer and a mixture thereof. For example, the thickening agent(s) includes or is selected from polyamide-8, hydrogenated styrene/isoprene copolymer, and a mixture thereof.

The amount of thickening agents in the skin tightening composition typically ranges from about 0.5 to about 35 wt. %, based on the total weight of the skin tightening composition. For example, the skin tightening composition may include thickening agents in an amount of about 1 to about 35 wt. %, about 2 to about 35 wt. %, about 3 to about 35 wt. %, about 4 to about 35 wt. %, about 5 to about 35 wt. %, about 6 to about 35 wt. %, about 8 to about 35 wt. %, about 10 to about 35 wt. %, about 14 to about 35 wt. %, about 18 to about 35 wt. %, about 22 to about 35 wt. %; about 1 to about 25 wt. %, about 2 to about 25 wt. %, about 3 to about 25 wt. %, about 4 to about 25 wt. %, about 6 to about 25 wt. %, about 8 to about 25 wt. %, about 10 to about 25 wt. %, about 14 to about 25 wt. %, about 18 to about 25 wt. %; about 1 to about 20 wt. %, about 2 to about 20 wt. %, about 3 to about 20 wt. %, about 4 to about 20 wt. %, about 6 to about 20 wt. %, about 8 to about 20 wt. %, about 10 to about 20 wt. %, about 14 to about 20 wt. %; about 1 to about 15 wt. %, about 2 to about 15 wt. %, about 3 to about 15 wt. %, about 4 to about 15 wt. %, about 6 to about 15 wt. %, about 8 to about 15 wt. %, about 10 to about 15 wt. %, including all ranges and subranges, based on the total weight of the skin tightening composition.

Non-limiting examples of thickening agents is provided below.

Mineral Thickening Agents

Mineral thickening agents are mineral based compounds that thicken or modify the viscosity of the skin tightening compositions. Non-limiting examples of mineral thickening agents include silica silylate, fumed silica, zeolite, natural clay, synthetic clay, kaolin, hectorite, organically modified hectorite (e.g., INCI: pentaerythrityl tetraisostearate (and) disteardimonium hectorite (and) propylene carbonate), an activated clay (e.g., disteardimonium hectorite, stearalkonium hectorite, quaternium-18 bentonite, quaternium-18 hectorite, and benzalkonium bentonite), and a mixture thereof.

In some instances, the skin tightening compositions may include one or more mineral thickening agents selected from optionally modified silicas, optionally modified clays, and a mixture thereof. The mineral thickening agents may be selected from optionally modified silicas, optionally modified clays, and a mixture thereof. In some instance, the mineral thickening agents are chosen from lipophilic (organophilic) clays, in particular modified hectorites; hydrophobic-treated fumed silica; hydrophobic silica aerogels, and mixtures thereof (e.g., disteardimonium hectorite, silica silylate, or a mixture thereof).

The mineral thickening agents may be selected from silica silylate, fumed silica, zeolite, natural clay, synthetic clay, kaolin, hectorite, organically modified hectorite (e.g., INCI: pentaerythrityl tetraisostearate (and) disteardimonium hectorite (and) propylene carbonate), an activated clay (e.g., disteardimonium hectorite, stearalkonium hectorite, quaternium-18 bentonite, quaternium-18 hectorite, and benzalkonium bentonite).

Optionally Modified Silicas

Optionally modified silicas include fumed silica optionally subjected to a hydrophobic surface treatment, the particle size of which may be less than 1 μm. Specifically, it is possible to chemically modify the surface of the silica, by chemical reaction generating a reduced number of silanol groups present at the surface of the silica. Silanol groups can in particular be replaced by hydrophobic groups: a hydrophobic silica is then obtained. The hydrophobic groups may be:

trimethylsiloxyl groups, which are obtained especially by treating fumed silica in the presence of hexamethyldisilazane. Silicas thus treated are known as "silica silylate" according to the CTFA (6th edition, 1995). They are sold, for example, under the references Aerosil R812 by the company Degussa, and Cab-O-Sil TS-53 by the company Cabot;

dimethylsilyloxyl or polydimethylsiloxane groups, which are obtained in particular by treating fumed silica in the presence of polydimethylsiloxane or dimethyldichlorosilane. Silicas thus treated are known as "silica dimethyl silylate" according to the CTFA (6th edition, 1995). They are sold, for example, under the references Aerosil R972 and Aerosil R974 by the company Degussa, and Cab-O-Sil TS-610 and Cab-O-Sil TS-720 by the company Cabot.

The hydrophobic fumed silica in particular may have a particle size that is nanometric to micrometric, for example ranging from about 5 to 200 nm.

The optionally modified silicas may, for instance, be silica aerogel particles. Silica aerogels are porous materials obtained by replacing (by drying) the liquid component of a silica gel with air. They are generally synthesized via a sol-gel process in a liquid medium and then dried, usually by extraction with a supercritical fluid, the one most commonly used being supercritical $CO_2$. This type of drying makes it possible to avoid shrinkage of the pores and of the material. The sol-gel process and the various drying processes are described in detail in Brinker C J., and Scherer G. W., Sol-Gel Science: New York: Academic Press, 1990.

The hydrophobic silica aerogel particles may have a specific surface area per unit mass ($S_M$) ranging from 500 to 1500 $m^2/g$, preferably from 600 to 1200 $m^2/g$ and better still from 600 to 800 $m^2/g$, and a size expressed as the volume mean diameter (D[0.5]) ranging from 1 to 1500 μm, better still from 1 to 1000 μm, preferably from 1 to 100 μm, in particular from 1 to 30 μm, more preferably from 5 to 25 μm, better still from 5 to 20 μm, and even better still from 5 to 15 μm. In some instances, the hydrophobic silica aerogel particles have a size expressed as volume-mean diameter (D[0.5]) ranging from 1 to 30 μm, preferably from 5 to 25 μm, better still from 5 to 20 μm and even better still from 5 to 15 μm.

The hydrophobic silica aerogel particles may have a specific surface area per unit mass ($S_M$) ranging from 600 to 800 $m^2/g$ and a size expressed as the volume mean diameter (D[0.5]) ranging from 5 to 20 μm and even better still from 5 to 15 μm. The hydrophobic silica aerogel particles may have a specific surface area per unit of volume $S_V$ ranging from 5 to 60 $m^2/cm^3$, preferably from 10 to 50 $m^2/cm^3$ and better still from 15 to 40 $m^2/cm^3$.

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups. In some instances, it is particularly useful to use hydrophobic silica aerogel particles surface-modified with trimethylsilyl groups. Mention may be made of the aerogels sold by the company Cabot under the references Aerogel TLD 201, Aerogel OGD 201, Aerogel TLD 203, Enova Aerogel MT 1100 and Enova Aerogel MT 1200. Particularly useful aerogels include hydrophobic silica aerogels, preferably of silyl silica (INCI name: silica silylate).

Optionally Modified Clays

Clays are silicates containing a cation that may be chosen from calcium, magnesium, aluminum, sodium, potassium and lithium cations, and mixtures thereof. Examples of such material include, but are not limited to clays of the smectite family, and also of the vermiculite, stevensite and chlorite families. These clays can be of natural or synthetic origin.

Mention may particularly be made of smectites, such as saponites, hectorites, montmorillonites, bentonites or beidellite and in particular synthetic hectorites (also known as laponites), such as the products sold by Rockwood Additives Limited under the names Laponite XLS, Laponite XLG, Laponite RD, Laponite RDS and Laponite XL21 (these products are sodium magnesium silicates and in particular sodium lithium magnesium silicates); bentonites, such as the product sold under the name Bentone HC by Rheox; magnesium aluminum silicates, which are in particular hydrated, such as the products sold by Vanderbilt Company under the name Veegum Ultra, Veegum HS or Veegum DGT, or also calcium silicates and in particular that in synthetic form sold by the company under the name Micro-Cel C.

In some instances, organophilic clays are preferred, more particularly modified clays, such as montmorillonite, bentonite, hectorite, attapulgite and sepiolite, and mixtures thereof. The clay may be optionally modified bentonite or an optionally modified hectorite. Clays may be modified with a chemical compound chosen from quaternary amines, tertiary amines, amine acetates, imidazolines, amine soaps, fatty sulfates, alkylarylsulfonates and amine oxides, and mixtures thereof.

Mention may be made of hectorites modified with a quaternary amine, more specifically with a $C_{10}$ to $C_{22}$ fatty acid ammonium halide, such as a chloride, such as hectorite modified with distearyldimethylammonium chloride (CTFA name: Disteardimonium hectorite), for instance the product sold under the name Bentone 38V, Bentone 38V CG or Bentone EW CE by the company Elementis, or stearalkonium hectorites, such as Bentone 27 V. In some instances, the clay is preferably disteardimonium hectorite.

Mention may also be made of quaternium-18 bentonites, such as those sold under the names Bentone 34 by the company Elementis, Tixogel VP by the company United Catalyst and Claytone 40 by the company Southern Clay; stearalkonium bentonites, such as those sold under the names Tixogel LG by the company United Catalyst and Claytone AF and Claytone APA by the company Southern Clay; or quaternium-18/benzalkonium bentonites, such as that sold under the name Claytone HT by the company Southern Clay. In some instances, it is preferable that the clay is chosen from organophilic modified clays, in particular organophilic modified hectorites, in particular modified with distearyldimethylammonium chloride (CTFA name: Disteardimonium hectorite).

Non-Mineral Thickening Agents

Non-mineral thickening agents, if present, may be lipophilic or hydrophilic, i.e., they may be appropriate for thickening an oily phase or an anhydrous composition or they may be appropriate for thickening an aqueous phase or an aqueous composition. For anhydrous compositions, lipophilic thickening agents or thickening agents that thicken anhydrous (e.g., oily) compositions are useful. Similarly, for aqueous compositions, hydrophilic thickening agents are useful.

Non-limiting examples of the non-mineral thickening agents useful for thickening anhydrous compositions include $C_{12-22}$ alkyl acrylate/hydroxyethylacrylate copolymer (INTELIMER), ethylene diamine/stearyl dimer dilinoleate copolymer such as OLEOCRAFT LP-10-PA-(MV) sold by Croda, polyamide-8 such as OLEOCRAFT LP-20-PA-(MV) sold by Croda, poly $C_{10}$-$C_{30}$ alkyl acrylate such as INTELIMER IPA 13-6 or INTELIMER IPA 13-1 NG Polymer sold by Air Products & Chemicals, nylon-611/dimethicone copolymer such as Dow Corning 2-8179 Gellant sold by Dow Corning, or dextrin palmitate such as RHEOPEARL KL2-OR sold by Chiba Flour Milling.

Additional non-limiting examples of non-mineral thickening agents useful for thickening anhydrous compositions include thickening polymers such as block copolymers of styrene with isoprene, butadiene, ethylene/propylene or ethylene/butylene including those presently available under the trade name KRATON, and particularly hydrogenated styrene/isoprene linear diblock copolymers. A related category of thickening polymer comprises polymers of alpha methylstyrene and styrene, such as those under the trade name KRISTALEX. Yet another thickening polymer comprises alkyl substituted galactomannan available under the trade name N-HANCE AG. Non-mineral thickening agents useful for thickening anhydrous compositions may also include thickening polymers such as vinyl pyrrolidone with polyethylene containing at least 25 methylene units, such as triacontanyl polyvinylpyrrolidone, under the trade name Antaron WP-660.

Non-limiting examples of non-mineral thickening agents may, optionally, be included for thickening aqueous compositions include xanthan gum, guar gum, biosaccharide gum, cellulose, acacia Seneca gum, sclerotium gum, agarose, pechtin, gellan gum, hyaluronic acid. Additionally, the one or more non-mineral thickening agents may be polymeric thickening agents such as, for example, ammonium polyacryloyldimethyl taurate, ammonium acryloyldimethyl-taurateA/P copolymer, sodium polyacrylate, acrylates copolymers, polyacrylamide, carbomer, and acrylates/C10-30 alkyl acrylate crosspolymer.

Additional, non-limiting examples of various types of non-mineral thickening agents include:

Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other carboxylic acid polymeric agents include Ultrez® 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickening agents useful herein are those selected from carbomers, acrylates/C10-C30 alkyl acrylate crosspolymers, and mixtures thereof.

Crosslinked Polyacrylate Polymers

The compositions of the present disclosure can optionally contain crosslinked polyacrylate polymers useful as thickening agents or gelling agents including both cationic and nonionic polymers. Examples of useful crosslinked nonionic polyacrylate polymers and crosslinked cationic polyacrylate polymers are those described in U.S. Pat. Nos. 5,100,660, 4,849,484, 4,835,206, 4,628,078 U.S. Pat. No. 4,599,379 and EP 228,868, which are all incorporated herein by reference in their entirety.

Polyacrylamide Polymers

The compositions of the present disclosure can optionally contain polyacrylamide polymers, especially nonionic polyacrylamide polymers including substituted branched or unbranched polymers. Among these polyacrylamide polymers is the nonionic polymer given the CTFA designation polyacrylamide and isoparaffin and laureth-7, available under the Tradename Sepigel 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

The compositions may also contain thickening and texturising gels of the type as exemplified by the product range called Lubrajel® from United Guardian. These gels have moisturizing, viscosifying, stabilizing properties.

Polysaccharides

A wide variety of polysaccharides can be useful herein. "Polysaccharides" refer to gelling agents that contain a backbone of repeating sugar (i.e., carbohydrate) units. Non-limiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-3) linked glucose units with a (1-6) linked glucose every three units, a commercially available example of which is Clearogel™, provided by CS11 from Michel Mercier Products Inc.

Gums

Other thickening and gelling agents useful herein include materials which are primarily derived from natural sources. Non-limiting examples of these thickening and/or gelling agent include gums such as those chosen from acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic hetero-polysaccharide derived from callus of plants belonging to *Polyantes* sp. (for example, tuberous polysaccharide), proteins (for example, sodium casein, gelatin, albumin), chondroitin sulfate, and hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

Silicone Elastomer(s)

The silicone elastomers can be non-emulsifying silicone elastomers, emulsifying silicone elastomers, or a mixture thereof. Non-emulsifying silicone elastomers include, but are not limited to, those organopolysiloxane elastomers not containing a hydrophilic chain, such as polyoxyalkylene or polyglycerolated chains. On the other hand, emulsifying silicone elastomers include, but are not limited to, polyoxyalkylenated silicone elastomers and a polyglycerolated silicone elastomers.

The total amount of silicone elastomers in the skin tightening compositions can vary but is typically about 1 to about 15 wt. %, based on the total weight of the skin tightening composition. In some cases, the total amount of silicone elastomers may be about 1 to about 15 wt. %, about 1 to about 10 wt. %, about 2 to about 40 wt. %, about 2 to about 35 wt. %, about 2 to about 30 wt. %, about 2 to about 25 wt. %, about 2 to about 20 wt. %, about 2 to about 15 wt. %, or about 2 to about 10 wt. %, based on the total weight of the skin tightening composition.

Non-Emulsifying Silicone Elastomers

The term "non-emulsifying" silicone elastomers defines organopolysiloxane elastomers not containing a hydrophilic chain, such as polyoxyalkylene or polyglycerolated chains.

Non-emulsifying silicone elastomers include elastomeric crosslinked organopolysiloxanes that can be obtained by a crosslinking addition reaction of diorganopolysiloxane containing at least one hydrogen bonded to silicon and of diorganopolysiloxane containing ethylenically unsaturated groups bonded to silicon, in particular in the presence of a platinum catalyst; or by a dehydrogenation crosslinking condensation reaction between a diorganopolysiloxane containing hydroxyl end groups and a diorganopolysiloxane containing at least one hydrogen bonded to silicon, in particular in the presence of an organotin; or by a crosslinking condensation reaction of a diorganopolysiloxane containing hydroxyl end groups and of a hydrolysable organopolysilane; or by thermal crosslinking of organopolysiloxane, in particular in the presence of an organoperoxide catalyst; or by crosslinking of organopolysiloxane via high-energy radiation such as gamma rays, ultraviolet rays or an electron beam.

A non-limiting example of a non-emulsifying silicone elastomer is dimethicone crosspolymer. In some instances, the non-emulsifying silicone elastomer is a cross-linked silicone, for example, dimethicone crosspolymer, (dimethicone/vinyl dimethicone) crosspolymer, (dimethicone/phenyl vinyl dimethicone) crosspolymer, (vinyl dimethicone/lauryl dimethicone) crosspolymer, (lauryl polydimethylsiloxyethyl dimethicone/bis-vinyl dimethicone) crosspolymer, alkyl (C30-45) cetearyl dimethicone crosspolymer, cetearyl dimethicone crosspolymer, and a mixture thereof. In some instances, dimethicone crosspolymer is particularly preferred.

In some instances, the elastomeric crosslinked organopolysiloxane is obtained by crosslinking addition reaction (A2) of diorganopolysiloxane containing at least two hydrogens each bonded to a silicon, and (B2) of diorganopolysiloxane containing at least two ethylenically unsaturated groups bonded to silicon, in particular in the presence (C2) of a platinum catalyst, as described, for example, in patent application EP295886, which is incorporated herein by reference in its entirety.

In some instances, the organopolysiloxane can be obtained by reaction of dimethylpolysiloxane containing dimethylvinylsiloxy end groups and of methylhydrogenopolysiloxane containing trimethylsiloxy end groups, in the presence of a platinum catalyst.

Compound (A2) is the base reactant for the formation of elastomeric organopolysiloxane, and the crosslinking is performed by an addition reaction of compound (A2) with compound (B2) in the presence of the catalyst (C2). Compound (A2) may be a diorganopolysiloxane containing at least two lower (for example $C_2$-$C_4$) alkenyl groups; the lower alkenyl group may be chosen from vinyl, allyl and propenyl groups. These lower alkenyl groups may be located in any position on the organopolysiloxane molecule, but are preferably located at the ends of the organopolysiloxane molecule. The organopolysiloxane (A2) may have a branched-chain, linear-chain, cyclic or networked structure, but the linear-chain structure is preferred. Compound (A2) may have a viscosity ranging from the liquid state to the gum state. Preferably, compound (A2) has a viscosity of at least 100 centistokes at 25° C.

The organopolysiloxanes (A2) may be chosen from methylvinylsiloxanes, methylvinylsiloxane-dimethyl-siloxane copolymers, dimethylpolysiloxanes containing dimethylvinylsiloxy end groups, copolymers of dimethyl-siloxane-methylphenylsiloxane containing dimethylvinyl-siloxy end groups, copolymers of dimethylsiloxane-diphenylsiloxane-methylvinylsiloxane containing dimethylvinylsiloxy end groups, copolymers of dimethyl-siloxane-methylvinylsiloxane containing trimethylsiloxy end groups, copolymers of dimethylsiloxane-methyl-phenylsiloxane-methylvinylsiloxane containing trimethylsiloxy end groups, methyl(3,3,3-trifluoro-propyl)polysiloxanes containing dimethylvinylsiloxy end groups, and copolymers of dimethylsiloxane-methyl-(3,3,3-trifluoropropyl)siloxane containing dimethylvinylsiloxy end groups.

Compound (B2) is in particular an organopolysiloxane containing at least 2 hydrogens bonded to silicon in each molecule and is thus the crosslinking agent for compound (A2).

In some instances, the sum of the number of ethylenic groups per molecule of compound (A2) and the number of hydrogen atoms bonded to silicon per molecule of compound (B2) is at least 4.

Compound (B2) may be in any molecular structure, in particular of linear-chain or branched-chain structure, or cyclic structure. Compound (B2) may have a viscosity at 25° C. ranging from 1 to 50000 centistokes, in particular so as to have good miscibility with compound (A). It is advantageous for compound (B2) to be added in an amount such that the molecular ratio between the total amount of hydrogen atoms bonded to silicon in compound (B2) and the total amount of all the ethylenically unsaturated groups in compound (A2) is within the range of from 1/1 to 20/1.

Compound (B2) may be chosen from methylhydrogenopolysiloxanes containing trimethylsiloxy end groups, copolymers of dimethylsiloxane-methylhydrogenosiloxane containing trimethylsiloxy end groups, and dimethyl-siloxane-methylhydrogenosiloxane cyclic copolymers.

Compound (C2) is the crosslinking reaction catalyst, and is in particular chloroplatinic acid, chloroplatinic acid-olefin complexes, chloroplatinic acid-alkenylsiloxane complexes, chloroplatinic acid-diketone complexes, platinum black, or platinum on a support.

The catalyst (C2) is preferably added at from 0.1 to 1000 parts by weight, better still from 1 to 100 parts by weight, as clean platinum metal per 1000 parts by weight of the total amount of compounds (A2) and (B2).

Other organic groups may be bonded to silicon in the organopolysiloxanes (A2) and (B2) described above, for instance alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

The non-emulsifying silicone elastomer according to the invention can be mixed with at least one hydrocarbon-based oil and/or one silicone oil so as to form a gel. In these gels, the non-emulsifying elastomer is often in the form of non-spherical particles.

Non-emulsifying elastomers that may be used include those sold under the names DOWSIL EL-8048 from DOW (INCI: Isododecane (and) Dimethicone Crosspolymer), KSG-6, KSG-15, KSG-16, KSG-18, KSG-41, KSG-42, KSG-43, KSG-44, USG-105 and USG-106 by the company Shin-Etsu, DC9040, DC9041, DC9509, DC9505, DC9506, DC5930, DC9350, DC9045 and DC9043 by the company Dow Corning, Gransil by the company Grant Industries, and SFE 839 by the company General Electric.

The total amount of non-emulsifying silicone elastomers in the skin tightening compositions, if present, may vary but is typically about 0.1 to about 20 wt. %, based on the total weight of the skin tightening composition. In some cases, the total amount of non-emulsifying silicone elastomers in the skin tightening compositions is about 0.1 to about 15 wt. %, about 0.1 to about 10 wt. %, about 0.1 to about 5 wt. %, about 1 to about 20 wt. %, about 1 to about 15 wt. %, about 1 to about 10 wt. %, or about 1 to about 5 wt. %, based on the total weight of the skin tightening composition.

Emulsifying Silicone Elastomers

The term "emulsifying silicone elastomer" is intended to mean a silicone elastomer comprising at least one hydrophilic chain. For example, emulsifying silicone elastomers may be chosen from polyoxyalkylenated silicone elastomers, polyglycerolated silicone elastomers, and a mixture thereof.

Polyoxyalkylenated Silicone Elastomers

A polyoxyalkylenated silicone elastomer may be a crosslinked organopolysiloxane that can be obtained by crosslinking addition reaction of diorganopolysiloxane containing at least one hydrogen bonded to silicon and of a polyoxyalkylene having at least two ethylenically unsaturated groups. In particular, the polyoxyalkylenated crosslinked organopolysiloxane may be obtained by crosslinking addition reaction (A1) of diorganopolysiloxane containing at least two hydrogens each bonded to a silicon, and (B1) of polyoxyalkylene containing at least two ethylenically unsaturated groups, in particular in the presence (C1) of a platinum catalyst, as described, for example, in U.S. Pat. Nos. 5,236,986 and 5,412,004, which are incorporated herein by reference in their entirety.

The organopolysiloxane can be obtained by reaction of polyoxyalkylene (in particular polyoxyethylene and/or polyoxypropylene) containing dimethylvinylsiloxy end groups and of methylhydrogeno-polysiloxane containing trimethylsiloxy end groups, in the presence of a platinum catalyst.

The organic groups bonded to silicon atoms of the compound (A1) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenyl-ethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

Compound (A1) may be chosen from methylhydrogenopolysiloxanes containing trimethylsiloxy end groups, copolymers of dimethylsiloxane-methylhydrogenosiloxane containing trimethylsiloxy end groups, cyclic dimethylsiloxane-methylhydrogenosiloxane copolymers, and copolymers of dimethylsiloxane-methylhydrogenosiloxane-laurylmethylsiloxane containing trimethylsiloxy end groups.

Compound (C1) is the crosslinking reaction catalyst, and is in particular chloroplatinic acid, chloroplatinic acid-olefin complexes, chloroplatinic acid-alkenylsiloxane complexes, chloroplatinic acid-diketone complexes, platinum black and platinum on a support.

In some cases, the polyoxyalkylenated silicone elastomers may be formed from divinyl compounds, in particular polyoxyalkylenes having at least two vinyl groups, reacting with Si—H bonds of a polysiloxane.

The polyoxyalkylenated silicone elastomers are often mixed with at least one hydrocarbon-based oil and/or one silicone oil so as to form a gel. In these gels, the polyoxyalkylenated elastomer can be in the form of non-spherical particles. Polyoxyalkylenated elastomers are in particular described in U.S. Pat. Nos. 5,236,986, 5,412,004, 5,837,793 and 5,811,487, which are incorporated herein by reference in their entirety. Further, useful polyoxyalkylenated silicone elastomers include, but are not limited to, those sold under the names KSG-21, KSG-20, KSG-30, KSG-31, KSG-32, KSG-33, KSG-210, KSG-310, KSG-320, KSG-330, KSG-340 and X-226146 by the company Shin-Etsu, and DC9010 and DC9011 by the company Dow Corning.

Polyglycerolated Silicone Elastomers

Polyglycerolated silicone elastomers are typically crosslinked elastomeric organopolysiloxanes that can be obtained by a crosslinking addition reaction of diorganopolysiloxane containing at least one hydrogen bonded to silicon and of polyglycerolated compounds having ethylenically unsaturated groups, often carried out in the presence of a platinum catalyst. For instance, in some cases, the crosslinked elastomeric organopolysiloxane is obtained by crosslinking addition reaction (A) of diorganopolysiloxane containing at least two hydrogens each bonded to a silicon, and (B) of glycerolated compounds having at least two ethylenically unsaturated groups, in particular in the presence (C) of a platinum catalyst. In some instances, the organopolysiloxane can be obtained by reaction of a polyglycerolated compound containing dimethylvinylsiloxy end groups and of methylhydrogenopolysiloxane containing trimethylsiloxy end groups, in the presence of a platinum catalyst.

Compound (A) is the base reactant for the formation of elastomeric organopolysiloxane and the crosslinking is performed by an addition reaction of compound (A) with compound (B) in the presence of the catalyst (C). Compound (A) may be, for example, an organopolysiloxane containing at least 2 hydrogen atoms bonded to different silicon atoms in each molecule. Compound (A) may have any molecular structure, in particular a linear chain or branched chain structure or a cyclic structure. Furthermore, compound (A) may have a viscosity at 25° C. ranging from 1 to 50,000 centistokes, in particular so as to have good miscibility with compound (B).

The organic groups bonded to the silicon atoms of compound (A) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group. In some instances, it is preferable that said organic group is chosen from methyl, phenyl and lauryl groups.

Compound (A) can thus be chosen from methylhydrogenopolysiloxanes containing trimethylsiloxy end groups, copolymers of dimethylsiloxane-methyl-hydrogenosiloxane containing trimethylsiloxy end groups, dimethylsiloxane-methylhydrogenosiloxane cyclic copolymers, and copolymers of dimethylsiloxane-methyl-hydrogenosiloxane-laurylmethylsiloxane containing trimethylsiloxy end groups.

Compound (B) may be a polyglycerolated compound corresponding to formula (B1) below:

$$C_mH_{2m-1}\text{—O—}[Gly]_n\text{-}C_mH_{2m-1} \quad (B')$$

in which m is an integer ranging from 2 to 6, n is an integer ranging from 2 to 200, preferably ranging from 2 to 100, preferably ranging from 2 to 50, preferably n ranging from 2 to 20, preferably from 2 to 10, and preferentially ranging from 2 to 5, and in particular equal to 3; Gly denotes:

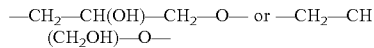

—CH$_2$—CH(OH)—CH$_2$—O— or —CH$_2$—CH(CH$_2$OH)—O—

Often, the sum of the number of ethylenic groups per molecule of compound (B) and of the number of hydrogen atoms bonded to silicon atoms per molecule of compound (A) is at least 4.

It can be advantageous for compound (A) to be added in an amount such that the molecular ratio between the total amount of hydrogen atoms bonded to silicon atoms in compound (A) and the total amount of all the ethylenically unsaturated groups in compound (B) is within the range of from 1/1 to 20/1.

Compound (C) is the crosslinking reaction catalyst, and is in particular chloroplatinic acid, chloroplatinic acid-olefin complexes, chloroplatinic acid-alkenylsiloxane complexes, chloroplatinic acid-diketone complexes, platinum black, or platinum on a support. The catalyst (C) is preferably added at from 0.1 to 1000 parts by weight, better still from 1 to 100 parts by weight, as clean platinum metal per 1000 parts by weight of the total amount of compounds (A) and (B).

The polyglycerolated silicone elastomers are often mixed with at least one hydrocarbon-based oil and/or one silicone oil so as to form a gel. In these gels, the polyglycerolated elastomer is often in the form of non-spherical particles. Such elastomers are in particular described in patent application WO 2004/024798, which is incorporated herein by reference in its entirety. As polyglycerolated silicone elastomers, mention may be made of those sold under the names KSG-710, KSG-810, KSG-820, KSG-830 and KSG-840 by the company Shin-Etsu.

The total amount of emulsifying silicone elastomers in the skin tightening compositions, if present, may vary but is typically about 0.1 to about 20 wt. %, based on the total weight of the skin tightening composition. In some cases, the total amount of emulsifying silicone elastomers in the skin tightening compositions is about 0.1 to about 15 wt. %, about 0.1 to about 10 wt. %, about 0.1 to about 5 wt. %, about 1 to about 20 wt. %, about 1 to about 15 wt. %, about 1 to about 10 wt. %, or about 1 to about 5 wt. %, based on the total weight of the skin tightening composition.

Volatile Hydrocarbon Oil(s)

The term "volatile hydrocarbon" is a hydrocarbon that is volatile at ambient temperature (25° C.) and normal pressure (1 atm) and may include, for example, isododecane, isohexadecane. The volatile hydrocarbons may be in the form of an oil. The term "oil" is understood to mean a compound which is liquid at ambient temperature (25° C.) and normal pressure (1 atm), and which, when it is introduced in a proportion of at least 1% by weight into water at 25° C. is not soluble in water or soluble to a level of less than 10% by weight, with respect to the weight of oil introduced into the water. The term "hydrocarbon oil" is oil comprising hydrogen and carbon atoms, and containing no silicon atoms.

Suitable volatile hydrocarbons include, but are not limited to, those having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of ISOPAR or PERMETHYL, the $C_8$ to $C_{16}$ branched esters such as isohexyl or isodecyl neopentanoate and their mixtures. Preferably, the volatile hydrocarbon oils have a flash point of below 60° C.

In some instances, the skin tightening composition includes at least one volatile hydrocarbon chosen from isoparaffin, isohexadecane, isododecane, isodecane, undecane, tridecane, dodecane, isohexyl, isodecyl, neopentanoate, or a combination thereof. In at least one instance, isododecane and/or isoparaffins (e.g., $C_{8-9}$ isoparaffin) are preferred. The skin tightening composition may be formulated to include volatile hydrocarbons that contain no silicon atoms.

The total amount of the volatile hydrocarbon may vary but is typically about 20 to about 85 wt. %, based on the total weight of the skin tightening composition. In some cases, the total amount of volatile hydrocarbons is about 20 to about 80 wt. %, about 20 to about 75 wt. %; about 25 to about 85 wt. %, about 25 to about 80 wt. %, about 25 to about 75 wt. %; about 30 to about 85 wt. %, about 30 to about 80 wt. %, about 30 to about 75 wt. %; about 35 to about 85 wt. %, about 35 to about 80 wt. %, about 35 to about 75 wt. %; about 40 to about 85 wt. %, about 40 to about 80 wt. %, about 40 to about 75 wt. %; about 45 to about 85 wt. %, about 45 to about 80 wt. %, about 45 to about 75 wt. %; about 50 to about 85 wt. %, about 50 to about 80 wt. %, about 50 to about 75 wt. %; about 55 to about 85 wt. %, about 55 to about 80 wt. %, about 55 to about 75 wt. %; about 60 to about 85 wt. %, about 60 to about 80 wt. %, about 60 to about 75 wt. %; about 65 to about 85 wt. %, about 65 to about 80 wt. %, or about 65 to about 75 wt. %, including ranges and subranges thereof, based on the total weight of the skin tightening composition.

The skin tightening composition may include a lower amount of volatile hydrocarbon oils (for example, when the skin tightening composition is an emulsion). For example, the amount of volatile hydrocarbon present in the skin tightening composition may be from about 20 to about 70 wt. %, about 25 to about 70 wt. %, about to about 70 wt. %, about 35 to about 70 wt. %, about 40 to about 70 wt. %, about 45 to about 70 wt. %, about 50 to about 70 wt. %, about 55 to about 70 wt. %; about 20 to about 60 wt. %, about 25 to about 60 wt. %, about 30 to about 60 wt. %, about 35 to about 60 wt. %, about 40 to about 60 wt. %, about 45 to about 60 wt. %, about 50 to about 60 wt. %; about 20 to about 55 wt. %, about 25 to about 55 wt. %, about 30 to about 55 wt. %, about 35 to about 55 wt. %, about 40 to about 55 wt. %, about 45 to about 55 wt. %, about 50 to about 55 wt. %; about 20 to about 50 wt. %, about 25 to about 50 wt. %, about 30 to about 50 wt. %, about 35 to about 50 wt. %, about 40 to about 50 wt. %, or about 45 to about 50 wt. %, including ranges and subranges thereof, based on the total weight of the skin tightening composition.

Filler(s)

The skin tightening composition includes at least one filler typically in an amount of about 0.5 to about 20 wt. %, based on the total weight of the skin tightening composition. The filler may be present in the skin tightening composition in an amount of about 0.5 to about 20 wt. %, about 1 to about 20 wt. %, about 1.5 to about 20 wt. %, about 2 to about 20 wt. %, about 2.5 to about 20 wt. %, about 3 to about 20 wt. %, about 3.5 to about 20 wt. %, about 4 to about 20 wt. %, about 4.5 to about 20 wt. %, about 5 to about 20 wt. %, about 6 to about 20 wt. %, about 7 to about 20 wt. %, about 8 to about 20 wt. %; about 1.5 to about 13 wt. %, about 1 to about 13 wt. %, about 1.5 to about 13 wt. %, about 2 to about 13 wt. %, about 2.5 to about 13 wt. %, about 3 to about 13 wt. %, about 3.5 to about 13 wt. %, about 4 to about 13 wt. %, about 4.5 to about 13 wt. %, about 5 to about 13 wt. %, about 6 to about 13 wt. %, about 7 to about 13 wt. %, about 8 to about 13 wt. %; about 0.5 to about 11 wt. %, about 1 to about 11 wt. %, about 1.5 to about 11 wt. %, about 2 to about 11 wt. %, about 2.5 to about 11 wt. %, about 3 to about 11 wt. %, about 3.5 to about 11 wt. %, about 4 to about 11 wt. %, about 4.5 to about 11 wt. %, about 5 to about 11 wt. %, about 6 to about 11 wt. %, about 7 to about 11 wt. %, about 8 to about 11 wt. %; about 0.5 to about 9 wt. %, about 1 to about 9 wt. %, about 1.5 to about 9 wt. %, about 2 to about 9 wt. %, about 2.5 to about 9 wt. %, about 3 to about 9 wt. %, about 3.5 to about 9 wt. %, about 4 to about 9 wt. %, about 4.5 to about 9 wt. %, about 5 to about 9 wt. %, about 6 to about 9 wt. %, about 7 to about 9 wt. %; about 0.5 to about 7 wt. %, about 1 to about 7 wt. %, about 1.5 to about 7 wt. %, about 2 to about 7 wt. %, about 2.5 to about 7 wt. %, about 3 to about 7 wt. %, about 3.5 to about 7 wt. %, about 4 to about 7 wt. %, about 4.5 to about 7 wt. %, or about 5 to about 7 wt. %, including all ranges and subranges thereof, based on the total weight of the skin tightening composition.

The at least one filler may be hydrophobic silica (such as, silica sylilate), silica, nylon-12, cellulose, methacrylate crosspolymer (such as, methyl methacrylate crosspolymer), silicone powder (such as, polymethylsisesquioxane), and a combination thereof.

In some instances, the skin tightening composition preferably includes a hydrophobic silica, such as silica sylilate. Hydrophobic silica are often provided in the form of particles, porous material obtained by replacing (by drying) the liquid component of a silica gel with air. They are generally synthesized via a sol-gel process in a liquid medium and then dried, usually by extraction with a supercritical fluid; the one most commonly used being supercritical $CO_2$. This type of drying makes it possible to avoid shrinkage of the pores and of the material. In some cases, the particles dissolve when combined with solvents.

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups. As regards the preparation of hydrophobic silica aerogel particles modified at the surface by silylation, reference may be made U.S. Pat. No. 7,470,725, incorporated herein by reference in its entirety. In some cases, useful hydrophobic silica particles are surface-modified with trimethylsilyl groups. In at least one instance, the hydrophobic silica is aerogel.

Hydrophobic silica include those that exhibit a specific surface area per unit of mass (SM) ranging from 500 to 1500 $m^2/g$, from 600 to 1200 $m^2/g$, or 600 to 800 $m^2/g$, and a size, expressed as the volume-mean diameter (D[0.5]), ranging from 1 to 1500 μm, from 1 to 1000 μm, or from 1 to 100 μm, in particular from 1 to 30 μm, from 5 to 25 μm, or from 5 to 20 μm, and in some cases from 5 to 15 μm. In some cases, the hydrophobic silica particles used in the skin tightening composition have a size, expressed as the volume-mean diameter (D[0.5]), ranging from 1 to 30 μm, from 5 to 25 μm, from 5 to 20 μm or from 5 to 15 μm. In some instances, the hydrophobic silica particles have a specific surface area per unit of mass (SM) ranging from 600 to 800 $m^2/g$ and a size expressed as the volume-mean diameter (D[0.5]) ranging from 5 to 20 μm or from 5 to 15 μm.

The specific surface area per unit of mass can be determined by the nitrogen absorption method, known as the BET (Brunauer-Emmett-Teller) method, described in The Journal of the American Chemical Society, Vol. 60, page 309, February 1938 and corresponding to the international standard ISO 5794/1 (appendix D). The BET specific surface area corresponds to the total specific surface area of the particles under consideration.

The sizes of hydrophobic silica particles (e.g., aerogel particles) can be measured by static light scattering using a commercial particle size analyzer of MasterSizer 2000 type from Malvern. The data are processed on the basis of the Mie scattering theory. This theory, which is exact for isotropic particles, makes it possible to determine, in the case of non-spherical particles, an "effective" particle diameter. This theory is described in particular in the publication by Van de Hulst, H. C., "Light Scattering by Small Particles", Chapters 9 and 10, Wiley, New York, 1957.

The hydrophobic silica particles may advantageously have a tapped density p ranging from 0.02 $g/cm^3$ to 0.10 $g/cm^3$, from 0.03 $g/cm^3$ to 0.10 $g/cm^3$, from 0.04 $g/cm^3$ to 0.10 $g/cm^3$, or from 0.05 $g/cm^3$ to 0.08 $g/cm^3$. The density p, known as the tapped density, may be assessed according to the following protocol: 40 g of powder are poured into a measuring cylinder; the measuring cylinder is then placed on a Stay 2003 machine from Stampf Volumeter; the measuring cylinder is then subjected to a series of 2500 packing motions (this operation is repeated until the difference in volume between two consecutive tests is less than 2 percent); the final volume Vf of packed powder is then measured directly on the measuring cylinder. The tapped density is determined by the ratio w/Vf, in this instance 40/Vf (Vf being expressed in $cm^3$ and w in g).

In some cases, the hydrophobic silica particles (e.g., aerogel particles) may have a specific surface area per unit of volume SV ranging from 5 to 100 $m^2/cm^3$, from 10 to 90 $m^2/cm^3$, from 15 to 40 $m^2/cm^3$, from 20 to 85 $m^2/cm^3$, or from 24 to 80 $m^2/cm^3$. The specific surface area per unit of volume is given by the relationship: $S_V=S_M \times \rho$, where ρ is the tapped density, expressed in $g/cm^3$, and $S_M$ is the specific surface area per unit of weight, expressed in $m^2/g$, as defined above.

The hydrophobic silica particles may have an oil-absorbing capacity, measured at the wet point, ranging from 5 to 18 ml/g, from 6 to 15 ml/g, or from 8 to 12 ml/g. The absorption capacity measured at the wet point, denoted Wp, corresponds to the amount of oil which is necessary to add to 100 g of particles in order to obtain a homogeneous paste. It is measured according to the "wet point" method or method of determination of oil uptake of a powder described in the standard NF T 30-022.

Mention may be made of hydrophobic silica sold under the name VM-2260 (INCI name: Silica silylate) by Dow Corning, the particles of which have a mean size of approximately 1000 microns and a specific surface area per unit of mass ranging from 600 to 800 m$^2$/g. Mention may also be made of the aerogels sold by Cabot under the references Aerogel TLD 201, Aerogel OGD 201, Aerogel TLD 203, Enova® Aerogel MT 1100 and Enova Aerogel MT 1200. Additionally, the hydrophobic silica aerogel particles sold under the name VM-2270 (INCI name: Silica silylate), by the company Dow Corning, the particles having an average size ranging from 5-15 microns and a specific surface area per unit of mass ranging from 600 to 800 m$^2$/g may be useful.

Additional fillers may include polyvalent silicates such as magnesium silicate, calcium silicate, aluminum silicate, a polyvalent silicate clay, montmorillonite, bentonite, smectite, and mixtures thereof. For instance, the filler may comprise magnesium aluminum silicate.

Fatty Compounds

In addition to the volatile hydrocarbon oils mentioned above, the skin tightening compositions may optionally include one or more fatty compounds, in particular, non-volatile fatty compound. The total amount of fatty compounds in the skin tightening compositions, if present, may vary but is typically about 0.1 to about 20 wt. %, based on the total weight of the skin tightening composition. In some cases, the total amount of emulsifying fatty compounds in the skin tightening compositions is about 0.1 to about 15 wt. %, about 0.1 to about 10 wt. %, about 0.1 to about 5 wt. %, about 1 to about 20 wt. %, about 1 to about 15 wt. %, about 1 to about 10 wt. %, about 1 to about 5 wt. %; about 2 to about 20 wt. %, about 2 to about 15 wt. %, about 2 to about 10 wt. %, about 2 to about 5 wt. %; about 4 to about 20 wt. %, about 4 to about 15 wt. %, about 4 to about 10 wt. %, about 4 to about 5 wt. %, including ranges and subranges thereof, based on the total weight of the skin tightening composition.

Non-limiting examples of non-volatile oils include:
 i. hydrocarbon oils of animal origin such as perhydrosqualene;
 ii. plant hydrocarbon oils, such as liquid triglycerides of fatty acids, for example sunflower oil, corn oil, soybean oil, marrow oil, grapeseed oil, sesame oil, hazelnut oil, apricot oil, macadamia oil, castor oil, avocado oil, caprylic/capric acid triglycerides;
 iii. oils of formula R$_9$COOR$_{10}$ in which R$_9$ represents a higher fatty acid residue containing from 7 to 19 carbon atoms and R$_{10}$ represents a branched hydrocarbon chain containing from 3 to 20 carbon atoms, such as, for example, Purcellin oil;
 iv. linear or branched hydrocarbons of mineral or synthetic origin, such as non-volatile liquid paraffins and derivatives thereof, petroleum jelly (petrolatum), polydecenes, and hydrogenated polyisobutene such as parleam;
 v. synthetic esters and ethers such as isopropyl myristate, octanoates, decanoates or ricinoleates of alcohols or of polyalcohols;
 vi. fatty alcohols such as octyidodecanol or oleyl alcohol;
 vii. partially hydrocarbonated and/or siliconated fluoro oils;
 viii. silicone oils such as linear, non-volatile polydimethylsiloxanes (dimethicone) which are liquid or pasty at room temperature, phenyldimethicones, phenyltrimethicones and polymethylphenylsiloxanes; and mixtures thereof.

In some instances, the one or more fatty substances may be selected form polyolefins (petrolatum), waxes, squalane, squalene, hydrogenated polyisobutene, hydrogenated polydecene, polybutene, mineral oil, pentahydrosqualene, dimethicone, and a mixture thereof.

Additional fatty compounds that are worth mentioning include fatty alcohols, fatty esters, fatty alcohols derivatives, fatty acid derivatives, such as those discussed below.

Fatty Alcohols

The one or more fatty compounds may be glycerolated and/or oxyalkylenated, include from 8 to 30 carbon atoms, and/or be saturated or unsaturated. The fatty alcohols useful herein include those having from about 8 to about 30 carbon atoms, from about 12 to about 22 carbon atoms, and from about 14 to about 22 carbon atoms. These fatty alcohols can be straight or branched chain alcohols and can be saturated or unsaturated. Non-limiting examples of fatty alcohols include decyl alcohol, undecyl alcohol, dodecyl alcohol, myristyl alcohol, cetyl alcohol, stearyl alcohol, isostearyl alcohol, isocetyl alcohol, behenyl alcohol, linalool, oleyl alcohol, cis4-t-butylcyclohexanol, myricyl alcohol and a mixture thereof. In some cases, the fatty alcohols comprise at least one of or may be chosen from myristyl alcohol, cetyl alcohol, stearyl alcohol, isostearyl alcohol, oleyl alcohol, isotridecyl alcohol, and a mixture thereof.

The saturated liquid fatty alcohols may be branched and optionally contain in their structure at least one aromatic or non-aromatic ring. In some instances, however, the fatty alcohols are acyclic. Non-limiting examples of liquid saturated fatty alcohols include octyldodecanol, isostearyl alcohol, and 2-hexyldecanol.

The unsaturated liquid fatty alcohol may include in their structure at least one double or triple bond. For example, the fatty alcohols may include several double bonds (such as 2 or 3 double bond), which may be conjugated or non-conjugated. The unsaturated fatty alcohols can be linear or branched and may be acyclic or include in their structure at least one aromatic or non-aromatic ring. Liquid unsaturated fatty alcohols may include or be chosen from oleyl alcohol, linoleyl alcohol, linolenyl alcohol and undecylenyl alcohol.

Non-limiting examples of solid fatty alcohols include linear or branched, saturated or unsaturated alcohols containing from 8 to 30 carbon atoms, for example, myristyl alcohol, cetyl alcohol, stearyl alcohol and their mixture, cetylstearyl alcohol.

Fatty Esters

The fatty compounds of the skin tightening composition may be liquid or solid fatty esters at 25° C. 1 atm. The fatty esters may include esters from a $C_6$-$C_{32}$ fatty acid and/or a $C_6$-$C_{32}$ fatty alcohol. For example, the fatty compounds may include or be chosen from fatty acid monoesters and diesters, polyol esters, polyglycerol esters, polyglycerol polyricinoleate, polyglycerol poly-12-hydroxystearate, polyglycerol dimerate isostearate, ethylhexanoate, polyglycerol esters, and a mixture thereof. These esters may be esters of saturated or unsaturated, linear or branched $C_1$-$C_{26}$ aliphatic mono or polyacids and of saturated or unsaturated, linear or branched $C_1$-$C_{25}$ aliphatic mono or polyalcohols, the total number of carbon atoms in the esters being greater than or equal to 10. In one instance, the fatty compounds comprise one or more fatty acid monoesters. For the esters of monoalcohols, at least one of the alcohol or the acid from which the esters result is branched. Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isononyl isononanoate, isodecyl neopentanoate and isostearyl neopentanoate.

In some instances, the fatty esters are cetyl esters, such as esters of saturated fatty acids and fatty alcohols. For example, the fatty esters may include or be chosen from cetyl palmitate, cetyl stearate, myristyl myristate, myristyl stearate, cetyl myristate, stearyl stearate, cetearyl ethylhexanoate, and mixtures thereof. In one instance, the fatty esters may be one or more of or chosen from isopropyl isostearate, n-propyl myristate, isopropyl myristate, hexyl laurate, hexadecyl isostearate, hexydecyl laurate, hexyldecyl octanoate, n-propyl palmitate, isopropyl palmitate, and mixtures thereof. In another instance, the fatty esters include or may be chosen from diisobutyl adipate, 2-hexyldecyl adipate, di-2-heptylundecyl adipate, monoisostearic acid N-alkyl glycol, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprate, triethyl citrate, 2-ethylhexyl succinate, isocetyl stearate, butyl stearate, diisopropyl sebacate, di-2-ethylhexyl sebacate, cetyl lactate, myristyl lactate, isopropyl palm itate, 2-ethylhexyl palm itate, 2-hexyldecyl palm itate, 2-heptylundecyl palm itate, cholesteryl 12-hydroxystearate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, diisostearyl malate, dicaprylyl carbonate, cetearyl ethylhexanoate, and mixtures thereof. In yet a further instance, the skin-tightening composition includes one or more of or may have fatty compounds chosen from cetearyl alcohol, cetearyl ethylhexanoate, isopropyl myristate, and mixtures thereof.

Non-limiting examples of solid fatty acid esters and/or fatty acid esters that may be mentioned include solid esters obtained from $C_9$-$C_{26}$ fatty acids and from $C_9$-$C_{25}$ fatty alcohols. Among these esters, mention may be made of octyldodecyl behenate, isocetyl behenate, cetyl lactate, stearyl octanoate, octyl octanoate, cetyl octanoate, decyl oleate, myristyl stearate, octyl palm itate, octyl pelargonate, octyl stearate, alkyl myristates such as cetyl myristate, myristyl myristate or stearyl myristate, and hexyl stearate.

Non-limiting examples of liquid fatty acid include triglyceride oils of plant or synthetic origin, such as liquid fatty acid triglycerides containing 6 to 30 carbon atoms, for instance heptanoic or octanoic acid triglycerides, or alternatively, e.g., sunflower oil, corn oil, soybean oil, marrow oil, grapeseed oil, sesame seed oil, hazelnut oil, apricot oil, macadamia oil, arara oil, castor oil, avocado oil, olive oil, rapeseed oil, coconut oil, wheatgerm oil, sweet almond oil, apricot oil, safflower oil, candlenut oil, coconut oil, camellina oil, tamanu oil, babassu oil and pracaxi oil, jojoba oil, shea butter oil, and mixtures thereof. In one instance, the one or more fatty compounds include at least one of or are selected from fatty acid triglycerides, oils, mineral oil, alkanes, fatty alcohols, fatty acids, fatty alcohol derivatives, alkoxylated fatty acids, polyethylene glycol esters of fatty acids, propylene glycol esters of fatty acids, butylene glycol esters of fatty acids, esters of neopentyl glycol and fatty acids, polyglycerol/glycerol esters of fatty acids, glycol diesters, diesters of ethylene glycol and fatty acids, esters of fatty acids and fatty alcohols, esters of short chain alcohols and fatty acids, esters of fatty alcohols, hydroxy-substituted fatty acids, waxes, and a mixture thereof. In another instance, fatty compounds of the skin-tightening composition includes one or more fatty acid triglycerides, such as caprylic/capric triglyceride.

Fatty Alcohol Derivatives

The skin-tightening compositions may, in some instances, include fatty alcohol derivatives such as alkyl ethers of fatty alcohols, alkoxylated fatty alcohols, alkyl ethers of alkoxylated fatty alcohols, esters of fatty alcohols and a mixture thereof. Non-limiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof. Liquid fatty ethers may be chosen from liquid dialkyl ethers such as dicaprylyl ether. The non-liquid fatty ethers may also be chosen from dialkyl ethers and in particular dicetyl ether and distearyl ether, alone or as a mixture.

Esters of $C_4$-$C_{22}$ dicarboxylic or tricarboxylic acids and of $C_1$-$C_{22}$ alcohols and esters of monocarboxylic, dicarboxylic or tricarboxylic acids and of $C_4$-$C_{26}$ dihydroxy, trihydroxy, tetrahydroxy or pentahydroxy non-sugar alcohols may also be used. Mention may be made in particular of diethyl sebacate; diisopropyl sebacate; diisopropyl adipate; di-n-propyl adipate; triisopropyl citrate; glyceryl trilactate; glyceryl trioctanoate; neopentyl glycol diheptanoate; and diethylene glycol diisononanoate.

Fatty Acid Derivatives

The skin-tightening compositions may, in some instances, include fatty acid derivatives. The fatty acid derivatives are defined herein to include fatty acid esters of the fatty alcohols as defined above, fatty acid esters of the fatty alcohol derivatives as discussed above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Non-limiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof.

Non-Ionic Surfactant(s)

The skin tightening composition may, optionally, include one or more nonionic surfactants. Although the skin tightening composition is typically an emulsion when containing one or more nonionic surfactants, the skin tightening composition may alternatively be anhydrous when containing such nonionic surfactants.

The nonionic surfactant(s) may include one or more of peg-30 dipolyhydroxystearate, polyglyceryl-4 diisostearate/polyhydroxystearate/sebacate, polyglyceryl-4 isostearate, polyglyceryl-2 dipolyhydroxystearate, dimethicone (and) peg/ppg-18/18 dimethicone, lauryl peg-9 polydimethylsiloxyethyl dimethicone, and a combination thereof. The nonionic surfactant can be, for example, selected from alcohols, alpha-diols, alkylphenols and esters of fatty acids, these compounds being ethoxylated, propoxylated or glycerolated and having at least one fatty chain comprising, for example, from 8 to 18 carbon atoms. The number of ethylene oxide or propylene oxide groups of the foregoing compounds may range from 2 to 50, and the number of glycerol groups may range from 1 to 30. Mention may be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol (C6-C24)alkylpolyglycosides; N—(C6-C24)alkylglucamine derivatives, amine oxides such as (C10-C14)alkylamine oxides or N—(C10-C14)acylaminopropylmorpholine oxides; and mixtures thereof. Maltose derivatives may also be mentioned.

The nonionic surfactants may be chosen from polyoxyalkylenated or polyglycerolated nonionic surfactants. The oxyalkylene units are more preferably oxyethylene or oxypropylene units, or a combination thereof, and are preferably oxyethylene units.

In some cases, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups—such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof. As glyceryl esters of fatty acids, glyceryl stearate (glyceryl mono-, di- and/or tristearate) (CTFA name: glyceryl stearate) or glyceryl ricinoleate and mixtures thereof can in particular be cited. As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited. Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEGIN by Goldschmidt (CTFA name: glyceryl stearate SE), can also be used.

Typically, the amount of nonionic surfactants included in the skin tightening compositions, when present, ranges from about 0.5 to about 10 wt. %, about 0.5 to about 8 wt. %, about 0.5 to about 6 wt. %, about 0.5 to about 5 wt. %, about 0.5 to about 4 wt. %; about 1 to about 10 wt. %, about 1 to about 8 wt. %, about 1 to about 6 wt. %, about 1 to about 5 wt. %, about 1 to about 4 wt. %; about 2 to about 10 wt. %, about 2 to about 8 wt. %, about 2 to about 6 wt. %, about 2 to about 5 wt. %, about 2 to about 4 wt. %; about 3 to about 10 wt. %, about 3 to about 8 wt. %, about 3 to about 6 wt. %, about 3 to about 5 wt. %, about 3 to about 4 wt. %, including all ranges and subranges thereof, based on the total weight of the skin tightening composition.

Dispersant(s)

The skin tightening composition may, optionally, include one or more dispersant. The dispersant may be chosen from olyoxyethylene glycol ethers or esters (POE/PEG ethers or esters) or polyoxypropylene glycol ethers or esters (PPG ethers or esters), from sugar ethers or esters, from glycerol or polyglycerol ethers or esters and from ethoxylated glyceride esters (POE glyceryl esters), polyhydroxystearic acid, or a combination thereof.

The dispersant may be selected such that it protects various ingredients of the skin tightening composition, such as coloring particles, that are solid at room temperature and atmospheric pressure against their aggregation or flocculation when it is placed in contact with an aqueous composition. More generally, the dispersant may be a surfactant, an oligomer, a polymer or a mixture of several thereof, bearing one or more functionalities that have strong affinity for the surface of the compounds to be dispersed. In some instances, the dispersant may be physically adsorbed onto the surface of the particles to be dispersed. In at least one instance, the dispersant is selected from those having a hydrophilicity with an HLB of 10 or less, 7 or less, or 6 or less. The term "HLB of 10 or less" means a surfactant having, at 25° C., an HLB balance (hydrophilic-lipophilic balance), within the Griffin meaning, of less than or equal to 10. The dispersant may be nonionic and/or chosen from polyoxyethylene glycol ethers or esters (POE/PEG ethers or esters) or polyoxypropylene glycol ethers or esters (PPG ethers or esters), from sugar ethers or esters, from glycerol or polyglycerol ethers or esters and from ethoxylated glyceride esters (POE glyceryl esters) or from mixtures thereof.

Typically, the amount of dispersants included in the skin tightening compositions, when present, ranges from about 0.1 to about 10 wt. %, 0.5 to about 10 wt. %, about 0.5 to about 8 wt. %, about 0.5 to about 6 wt. %, about 0.5 to about 5 wt. %, about 0.5 to about 4 wt. %; about 1 to about 10 wt. %, about 1 to about 8 wt. %, about 1 to about 6 wt. %, about 1 to about 5 wt. %, about 1 to about 4 wt. %; about 1.5 to about 10 wt. %, about 1.5 to about 8 wt. %, about 1.5 to about 6 wt. %, about 1.5 to about 5 wt. %, about 1.5 to about 4 wt. %, including all ranges and subranges thereof, based on the total weight of the skin tightening composition.

Water-Soluble Solvents

The skin tightening composition may optionally include one or more water-soluble solvents. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water soluble solvent has a solubility of at least 60%, 70%, 80%, or 90%. Non-limiting examples of water-soluble solvents include, for example, glycerin, $C_{1-4}$ alcohols, organic solvents, fatty alcohols, fatty ethers, fatty esters, polyols, glycols, and any a mixture thereof. In some instances, the skin tightening composition includes one or more $C_{1-4}$ alcohols, for example, ethanol.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

The total amount of the water-soluble solvents in the skin tightening composition, if present, may vary but is typically about 0.01 to about 25 wt. %, based on the total weight of the skin tightening composition. In some cases, the total amount of water-soluble solvents is about 0.01 to about 20 wt. %, about 0.01 to about 15 wt. %, about 0.01 to about 10 wt. %, about 0.1 to about 25 wt. %, about 0.1 to about 20 wt. %, about 0.1 to about 15 wt. %, about 0.1 to about 10 wt. %, about 1 to about 25 wt. %, about 1 to about 20 wt. %, about 1 to about 15 wt. %, about 1 to about 10 wt. %, or about 1 to about 8 wt. %, including all ranges and subranges thereof, based on the total weight of the skin tightening composition.

Inorganic Pigments

The skin tightening compositions may optionally include one or more inorganic pigments. Non-limiting examples include titanium dioxide, zirconium oxide, cerium oxide, zinc oxide, iron oxide, mica, alumina, aluminum hydroxide, chromium oxide, manganese violet, ultramarine blue, chromium hydrate, ferric blue, aluminum powder, copper powder, silver powder, gold powder, barium sulfate, carbon black, mica and mixtures thereof.

The total amount of inorganic pigments, if present, may vary but is typically about 0.01 to about 20 wt. %, based on the total weigh of the skin tightening composition. The total amount of inorganic pigments may be about 0.01 to about 20 wt. %, about 0.01 to about 18 wt. %, about 0.01 to about 16 wt. %, about 0.01 to about 14 wt. %, about 0.01 to about 12 wt. %, about 0.01 to about 10 wt. %, about 0.01 to about 8 wt. %, about 0.01 to about 6 wt. %, about 0.01 to about 5 wt. %, about 0.01 to about 4 wt. %, about 0.1 to about 10 wt. %, about 0.1 to about 8 wt. %, about 0.1 to about 5 wt. %, or about 0.1 to about 4 wt. %, about 1 to about 20 wt. %, about 1 to about 18 wt. %, about 1 to about 16 wt. %, about 1 to about 14 wt. %, about 1 to about 12 wt. %, about 1 to about 10 wt. %, about 1 to about 8 wt. %, about 2 to about 20 wt. %, about 2 to about 18 wt. %, about 2 to about 16 wt. %, about 2 to about 14 wt. %, about 2 to about 12 wt. %, about 2 to about 10 wt. %, about 2 to about 8 wt. %, about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. %, including ranges and subranges thereof, based on the total weight of the skin tightening composition.

Organic Colorants

The skin tightening compositions may optionally include one or more organic colorants. Non-limiting examples include D & C red no. 19 (CI 45,170), D & C red no. 9 (CI 15,585), D & C red no. 21 (CI 45,380), D & C orange no. 4 (CI 15,510), D & C orange no. 5 (CI 45,370), D & C red no. 27 (CI 45,410), D & C red no. 13 (CI 15,630), D & C red no. 7 (CI 15,850:1), D & C red no. 6 (CI 15,850:2), D & C yellow no. 5 (CI 19,140), D & C red no. 36 (CI 12,085), D & C orange no. 10 (CI 45,425), D & C yellow no. 6 (CI 15,985), D & C red no. 30 (CI 73,360), D & C red no. 3 (CI 45,430), carbon black (CI 77,266), cochineal carmine lake (CI 75,470), natural or synthetic melanin, and aluminum lakes.

The total amount of organic colorants, if present, may vary but is typically about 0.01 to about 20 wt. %, based on the total weigh of the skin tightening composition. The total amount of organic colorants may be about 0.01 to about 20 wt. %, about 0.01 to about 18 wt. %, about 0.01 to about 16 wt. %, about 0.01 to about 14 wt. %, about 0.01 to about 12 wt. %, about 0.01 to about 10 wt. %, about 0.01 to about 8 wt. %, about 0.01 to about 6 wt. %, about 0.01 to about 5 wt. %, about 0.01 to about 4 wt. %, about 0.1 to about 10 wt. %, about 0.1 to about 8 wt. %, about 0.1 to about 5 wt. %, or about 0.1 to about 4 wt. %, about 1 to about 20 wt. %, about 1 to about 18 wt. %, about 1 to about 16 wt. %, about 1 to about 14 wt. %, about 1 to about 12 wt. %, about 1 to about 10 wt. %, about 1 to about 8 wt. %, about 2 to about 20 wt. %, about 2 to about 18 wt. %, about 2 to about 16 wt. %, about 2 to about 14 wt. %, about 2 to about 12 wt. %, about 2 to about 10 wt. %, about 2 to about 8 wt. %, about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. %, including ranges and subranges thereof, based on the total weight of the skin tightening composition.

Soft Focus Powder

The skin tightening compositions may, optionally, include soft focus powder. Soft focus powders are materials providing a blurring effect, typically due to their light-scattering properties on the skin. Such powders typically have high diffuse reflectance, low specular reflectance, and high diffuse transmittance. Soft focus powders give the skin a smoother appearance, for example, by reducing the difference in luminosity between the valley and the edges of wrinkles and imperfections.

Non-limiting examples of soft focus powders include powders of natural or synthetic origin such as mica, titanated mica, alumina, titanium dioxide, serecite, composite talc/titanium dioxide/alumina/silica powders, polyamide, poly(methyl (meth)acrylate), polyethylene powder, polymethylsilsesquioxane powder, sodium acrylates crosspolymer-2 and a mixture thereof. Additional non-limiting examples include calcium aluminum borosilicate (LUXSIL), PMMA (Microsphere M-100), polyethylene (POLYETHYLENE CI 2080), methyl methacrylate crosspolymer (COVABEADS LH85), nylon-12 (ORGASOL 2002), or ethylene/acrylic acid copolymer (FLOBEADS EA209). In some instances, the skin tightening compositions include at least one soft focus powder selected from the group consisting of silica which may or may not be coated, fumed silica, silica silylate, composite talc/titanium dioxide/alumina/silica powders, polyamide (nylon), poly(methyl (meth)acrylate), polyethylene powder, polymethylsilsesquioxane powder, waxes, such as copernicia cerifera (carnauba) wax, dimethicone/vinyl dimethicone crosspolymer, nylon-12, cellulose, polylactic acid, boron nitride, and a mixture thereof. The copernicia cerifera (carnauba) wax can be provided as a dispersion non-water and alcohol. The dimethicone/vinyl dimethicone crosspolymer can be provided as silicone dispersion (INCI: Dimethicone/vinyl dimethicone crosspolymer (and) C12-14 Pareth-12). In some instances, the soft focus powder is (or includes) sodium acrylates crosspolymer-2, which is commercially available as AQUAKEEP 10SH-NFC as sodium acrylates crosspolymer-2 (and) water (and) silica.

The total amount of soft focus powder, if present, can vary but is typically about 0.1 to about 20 wt. %, based on the total weight of the skin tightening composition. In some cases, the total amount of soft focus powder is about 0.1 to about 20 wt. %, about 0.1 to about 18 wt. %, about 0.1 to about 16 wt. %, about 0.1 to about 15 wt. %, about 0.1 to about 14 wt. %, about 0.1 to about 12 wt. %, about 0.1 to about 10 wt. %, about 0.1 to about 5 wt. %, about 1 to about 20 wt. %, about 1 to about 18 wt. %, about 1 to about 16 wt. %, about 1 to about 15 wt. %, about 1 to about 14 wt. %, about 1 to about 12 wt. %, about 1 to about 10 wt. %, or about 1 to about 8 wt. %, about 2 to about 20 wt. %, about 2 to about 18 wt. %, about 2 to about 16 wt. %, about 2 to about 14 wt. %, about 2 to about 12 wt. %, about 2 to about 10 wt. %, about 2 to about 8 wt. %, about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. %, including ranges and subranges thereof, based on the total weight of skin tightening composition.

Skin Active Agents

The skin tightening compositions may, optionally, include one or more skin active agents, such as anti-aging agent, anti-wrinkle actives, anti-oxidants, humectants, moisturizing ingredients, depigmenting agents, and/or agents for treating oily skin etc. The skin active agents may be included in the skin tightening composition in an amount ranging from greater than zero to about to about 10 wt. %, based on the total weight of the composition. For example, the total amount of skin active agents may be from greater than zero to about 9 wt. %, greater than zero to about 8 wt. %, greater than zero to about 7 wt. %, greater than zero to about 6 wt. %, greater than zero to about 5 wt. %, greater than zero to about 4 wt. %, greater than zero to about 3 wt. %, greater than zero to about 2 wt. %; about 10 ppm to about 10 wt. % (100,000 ppm), about 10 ppm to about 5 wt. % (50,000 ppm), about 10 ppm to about 2.5 wt. % (25,000 ppm), about 10 ppm to about 1 wt. % (10,000 ppm), about 10 ppm to about 0.5 wt. % (5,000 ppm), about 10 ppm to about 0.3 wt. % (3,000 ppm), about 10 ppm to about 0.2 wt. % (2,000 ppm), about 10 ppm to about 0.1 wt. % (1,000 ppm), about 10 ppm to 500 ppm; about 0.1 to about 10 wt. %, about 0.1 to about 5 wt. %, about 0.1 to about 2.5 wt. %, about 0.1 to about 1 wt. %, about 0.1 to about 0.5 wt. %; about 1 to about 10 wt. %, about 1 to about 8 wt. %, about 1 to about 6 wt. %, about 1 to about 5 wt. %, about 1 to about 4 wt. %, about 1 to about 3 wt. %; about 2 to about 10 wt. %, about 2 to about 8 wt. %, about 2 to about 6 wt. %, about 2 to about 5 wt. %, about 2 to about 4 wt. %; about 3 to about 10 wt. %, about 3 to about 8 wt. %, about 3 to about 6 wt. %, about 3 to about 5 wt. %; about 4 to about 10 wt. %, about 4 to about 8 wt. %, or about 4 to about 6 wt. %, including ranges and subranges therebetween, based on the total weight of the skin tightening composition.

A non-limiting discussion of skin active agents that may, in some cases, be included in the skin tightening composition is provided below:

Humectants and/or Moisturizing Ingredients

Examples of humectants and/or moisturizing ingredients include glycerol and its derivatives, urea and its derivatives, especially Hydrovance marketed by National Starch, lactic acid, hyaluronic acid, AHA, BHA, sodium pidolate, xylitol, serine, sodium lactate, ectoin and its derivatives, chitosan and its derivatives, collagen, plankton, an extract of *Imperata cylindra* sold under the name Moist 24 by Sederma, homopolymers of acrylic acid as Lipidure-HM of NOF Corporation, beta-glucan and in particular sodium carboxymethyl beta-glucan Mibelle-AG-Biochemistry, a mixture of oils passionflower, apricot, corn, and rice bran sold by Nestle under the name NutraLipids, a C-glycoside derivatives, in particular the C-13-D-xylopyranoside-2-hydroxypropane in the form of a solution at 30% by weight of active material in a water/propylene glycol mixture (60/40 wt %) as the product produced by the company Chimex under the trade name "Mexoryl SBB", a rose hip oil marketed by Nestle, a micro-algae extract *Prophyridium cruentum* enriched with zinc, marketed under the name by Vincience Algualane Zinc spheres of collagen and chondroitin sulfate of marine origin (Atelocollagen) sold by the company Engelhard Lyon under the name Marine Filling Spheres, hyaluronic acid spheres such as those marketed by Engelhard Lyon, and arginine.

Depigmenting Agents

Depigmenting agents that may be incorporated in the skin tightening composition include those chosen from alpha and beta arbutin, ferulic acid, lucinol and its derivatives, kojic acid, resorcinol and derivatives thereof, tranexamic acid and derivatives thereof, gentisic acid, homogentisic, methyl gentisate or homogentisate, dioic acid, D pantheteine calcium sulphonate, lipoic acid, ellagicacid, vitamin B3, linoleic acid and its derivatives, certain compounds derived from plants such as chamomile, bearberry, the aloe family (vera, ferox, bardensis), mulberry, skullcap, a water kiwi fruit (*Actinidia chinensis*) marketed by Gattefosse, an extract of *Paeonia suffruticosa* root, such as that sold by Ichimaru Pharcos under the name Liquid Botanpi Be an extract of brown sugar (*Saccharum officinarum*) such as molasses extract marketed by Taiyo Kagaku under the name Liquid Molasses, without this list being exhaustive. Particular depigmenting agents include alpha and beta arbutin, ferulic acid, kojicacid, resorcinol and derivatives, D pantheteine calcium sulfonate, lipoic acid, ellagic acid, vitamin B3, a water kiwi fruit (*Actinidia chinensis*) marketed by Gattefosse, an extract of *Paeonia suffruticosa* root, such as that sold by the company Ichimaru Pharcos under the name Botanpi Liquid B.

Anti-Wrinkle Active

The skin tightening composition may include one or more anti-wrinkle actives. The term "anti-wrinkle active" refers to a natural or synthetic compound producing a biological effect, such as the increased synthesis and/or activity of certain enzymes, when brought into contact with an area of wrinkled skin, this has the effect of reducing the appearance of wrinkles and/or fine lines. Exemplary anti-wrinkle actives may be chosen from: desquamating agents, anti-glycation agents, inhibitors of NO-synthase, agents stimulating the synthesis of dermal or epidermal macromolecules and/or preventing their degradation, agents for stimulating the proliferation of fibroblasts and/or keratinocytes, or for stimulating keratinocyte differentiation reducing agents; muscle relaxants and/or dermo-decontracting agents, anti-free radical agents, and mixtures thereof. Examples of such compounds are: adenosine and its derivatives and retinoids other than retinol (as discussed above, such as retinol palmitate), ascorbic acid and its derivatives such as magnesium ascorbyl phosphate and ascorbyl glucoside; nicotinic acid and its precursors such as nicotinamide; ubiquinone; glutathione and precursors thereof such as L-2-oxothiazolidine-4-carboxylic acid, the compounds C-glycosides and their derivatives as described in particular in EP-1345919, in particular C-beta-D-xylopyranoside-2-hydroxy-propane as described in particular in EP-1345919, plant extracts including sea fennel and extracts of olive leaves, as well as plant and hydrolysates thereof such as rice protein hydrolysates or soybean proteins; algal extracts and in particular *laminaria*, bacterial extracts, the sapogenins such as diosgenin and extracts of *Dioscorea* plants, in particular wild yam, comprising: the a-hydroxy acids, f3-hydroxy acids, such as salicylic acid and n-octanoyl-5-salicylic oligopeptides and pseudodipeptides and acyl derivatives thereof, in particular acid {2-[acetyl-(3-trifluoromethyl-phenyl)-amino]-3-methyl-}acetic acid and lipopeptides marketed by the company under the trade names SEDERMA Matrixyl 500 and Matrixyl 3000; lycopene, manganese salts and magnesium salts, especially gluconates, and mixtures thereof. In at least one case, the skin tightening composition includes adenosine derivatives, such as non-phosphate derivatives of adenosine, such as in particular the 2'-deoxyadenosine, 2',3'-adenosine isopropoylidene; the toyocamycine, 1-methyladenosine, N-6-methyladenosine; adenosine N-oxide, 6-methylmercaptopurine riboside, and the 6-chloropurine riboside. Other derivatives include adenosine receptor agonists such as adenosine phenylisopropyl ("PIA"), 1-methylisoguanosine, N6-cyclohexyladenosine (CHA), N6-cyclopentyladenosine (CPA), 2-chloro-N6-cyclopentyladenosine, 2-chloroadenosine, N6-phenyladenosine, 2-phenylaminoadenosine, MECA, N 6-phenethyladenosine, 2-p-(2-carboxyethyl) phenethyl-amino-5'-N-ethylcarboxamido adenosine (CGS-21680), N-ethylcarboxamido-adenosine (NECA), the 5'(N-cyclopropyl)-carboxamidoadenosine, DPMA (PD 129.944) and metrifudil.

Skin Active Agent for Oily Skin

The skin tightening composition may, optionally, include a skin active agent that addresses oily skin. These agents can be sebo-regulating or antiseborrhoeic agents capable of regulating the activity of sebaceous glands. Exemplary skin active agents for addressing oily skin include: retinoic acid, benzoyl peroxide, sulfur, vitamin B6 (pyridoxine or) chloride, selenium, samphire—the cinnamon extract blends, tea and octanoylglycine such as—15 Sepicontrol A5 TEA from Seppic—the mixture of cinnamon, sarcosine and octanoylglycine marketed especially by Seppic under the trade name Sepicontrol A5—zinc salts such as zinc gluconate, zinc pyrrolidonecarboxylate (or zinc pidolate), zinc lactate, zinc aspartate, zinc carboxylate, zinc salicylate 20, zinc cysteate;—derivatives particularly copper and copper pidolate as Cuivridone Solabia-extracts from plants of *Arnica montana, Cinchona succirubra, Eugenia caryophyllata, Humulus lupulus, Hypericum perforatum, Mentha pipenta* 25 *Rosmarinus officinalis, Salvia officinalis* and *Thymus vulgaris*, all marketed for example by Maruzen—extracts of meadowsweet (*Spiraea ulmaria*), such as that sold under the name Sebonormine by Silab—extracts of the alga *Laminaria saccharina*, such as that sold under the 30 name Phlorogine by Biotechmarine—the root extracts of burnet mixtures (*Sanguisorba officinalis/Poterium officinale*), rhizomes of ginger (*Zingiber officinalis*) and cinnamon bark (*Cinnamomum cassia*), such as that sold under the name Sebustop by Solabia—extracts of flaxseed such as that sold under the name Linumine by Lucas Meyer—*Phellodendron* extracts such as those sold under the name *Phellodendron* extract BG by Maruzen or Oubaku liquid B by Ichimaru Pharcos—of argan oil mixtures extract of *Serenoa serrulata* (saw palmetto) extract and sesame seeds such as that sold under the name Regu SEB by Pentapharm—mixtures of extracts of willowherb, of *Terminalia chebula*, nasturtium and of bioavailable zinc (microalgae), such as that sold under the name Seborilys Green Tech;—extracts of *Pygeum afrianum* such as that sold under the name *Pygeum afrianum* sterolic lipid extract by Euromed—extracts of *Serenoa serrulata* such as those sold under the name Viapure Sabal by Actives International, and those sold by the company Euromed—of extracts of plantain blends, *Berberis aquifolium* and sodium salicylate 20 such as that sold under the name Seboclear Rahn—extract of clove as that sold under the name Clove extract powder by Maruzen—argan oil such as that sold under the name Lipofructyl Laboratories Serobiologiques; 25—lactic protein filtrates, such as that sold under the name Normaseb by Sederma—the seaweed *laminaria* extracts, such as that sold under the name Laminarghane by Biotechmarine—oligosaccharides seaweed *Laminaria digitata*, such as that sold under the name Phycosaccharide 30 AC by the company Codif—extracts of sugar cane such as that sold under the name Policosanol by the company Sabinsa, the sulfonated shale oil, such as that sold under the name Ichtyol Pale by Ichthyol—extracts of meadowsweet (*Spiraea ulmaria*) such as that sold under the name Cytobiol Ulmaire by societeLibiol—sebacic acid, especially sold in the form of a sodium polyacrylate gel under the name Sebosoft by Sederma—glucomannans extracted from konjac tuber and modified with alkylsulfonate chains such as that sold under the name Biopol Beta by Arch Chemical—extracts of *Sophora angustifolia*, such as those sold under the name *Sophora* powder or *Sophora* extract by Bioland—extracts of *cinchona* bark succirubra such as that sold under the name Red Bark HS by Alban Muller—extracts of *Quillaja saponaria* such as that sold under the name 15 Panama wood HS by Alban Muller—glycine grafted onto an undecylenic chain, such as that sold under the name Lipacide UG OR by SEPPIC—the mixture of oleanolic acid and nordihydroguaiaretic acid, such as that sold under the form of a gel under the name AC.Net by Sederma; 20—phthalimidoperoxyhexanoic acid-citrate tri (C12-C13) sold under the name COSMACOL® ECI by Sasol; trialkyl citrate (C14-C15) sold under the name COSMACOL® ECL by Sasol—10-hydroxydecanoic acid, including mixtures acid-hydroxydecanoic October 25, sebacic acid and 1,10-decandiol such as that sold under the name Acnacidol BG by Vincience and mixtures thereof.

Antioxidants

Vitamin C and derivatives may be used, including ascorbic acid, sodium ascorbate, and the fat soluble esters tetrahexyldecyl ascorbate and ascorbyl palmitate, magnesium ascorbyl phosphate, ascorbyl-glucoside, glucosamine ascorbate, ascorbyl acetate, etc. Additionally, extracts from plants containing a high amount of vitamin C such as camu berry (*Myrciaria dubia*), acerola, *Emblica officinalis*, and bioflavonoids from rose hip and citrus may be used including watersoluble bioflavonoids such as hesperidin methyl chalcone may also be used.

Sesame (*Sesamum indicum*) or sesame lignan may also be added. Sesame and its lignans (the fibrous compounds associated with the sesame) act as antioxidants. Sesame seed lignans significantly enhance vitamin E activity.

Other antioxidants include tocopherols (e.g. d-α-tocopherol, d-β-tocopherol, d-γ-tocopherol, d-delta-tocopherol), tocotrienols (e.g. d-α-tocotrienol, d-β-tocotrienol, d-γ.-tocotrienol, d-delta-tocotrienol) and vitamin E (α-tocopherol acetate). These compounds may be isolated from natural sources, prepared by synthetic means, or mixtures thereof. Tocotrienol-enriched vitamin E preparations may be obtained by fractionating vitamin E preparations to remove a portion of tocopherols and recover a preparation more highly concentrated in tocotrienol. Useful tocotrienols are natural products isolated, for example, from wheat germ oil, grain, or palm oil using high performance liquid chromatography, or isolated by alcohol extraction and/or molecular distillation from barley, brewer's grain or oats. As used herein, the term "tocotrienols" includes tocotrienol-rich fractions obtained from these natural products as well as the pure compounds. The increased glutathione peroxidase activity protects the skin from oxidative damage.

In addition, carotenoids, particularly the xanthophyll type, are also useful antioxidants that can be used. The xanthopyll type carotenoids include molecules, such as lutein, canthaxantin, cryptoxanthin, zeaxanthin and astaxanthin. Xanthophylls protect compounds, such as vitamin A, vitamin E, and other carotenoids.

Flavonoids

The active agent may be an antioxidant selected from the group of flavonoids. In some instances, the flavonoid is a flavanone (derivative of 2,3-dihydro-2-phenylchromen-4-one). Flavones include: Butin, Eriodictyol, Hesperetin, Hesperidin, Homoeriodictyol, Isosakuranetin, Naringenin, Naringin, Pinocembrin, Poncirin, Sakuranetin, Sakuranin, and Sterubin. The flavonoid may be a flavanonol (derivative of 3-hydroxy-2,3-dihydro-2-phenylchromen-4-one). Flavanols include: Taxifolin, Aromadedrin, Chrysandroside A, Chrysandroside B, Xeractinol, Astilbin, and Fustin. The flavonoid may be a flavone (derivative of 2-phenylchromen-4-one). Flavones include: Apigenin, Luteolin, Tangeritin, Chrysin, Baicalein, Scutellarein, Wogonin, Synthetic Flavones: Diosmin, and Flavoxate. The flavonoid may be a flavonol (derivative of 3-hydroxy-2-phenylchromen-4-one). Flavonols include: 3-Hydroxyflavone, Azaleatin, Fisetin, Galangin, Gossypetin, Kaempferide, Kaempferol, Isorhamnetin, Morin, Myricetin, Natsudaidain, Pachypodol, Quercetin, Rhamnazin, Rhamnetin, Azalein, Flyperoside, Isoquercitin, Kaempferitrin, Myricitrin, Quercitrin, Robinin, Rutin, Spiraeoside, Xanthorhamnin, Amurensin, Icariin, and Troxerutin. The flavonoid may be a flavan-3-ol (derivatives of 2-phenyl-3,4-dihydro-2H-chromen-3-ol). Flavan-3-ols include: Catechin, Epicatechin, Epigallocatechin, Epicatechin gallate, Epigallocatechin gallate, Epiafzelechin, Fisetinidol, Guibourtinidol, Mesquitol, and Robinetinidol. The flavonoid may be a flavan-4-ol (derivative of 2-phenylchroman-4-ol). Flavan-4-ols include: Apiforol and Luteoforol. The flavonoid may be an isoflavone (derivative of 3-phenylchromen-4-one). Isoflavones include: Genistein, Daidzein, Biochanin A, Formononetin, and the Equol metabolite from Daidzein.

The antioxidant may be an anthocyanidin (derivative of 2-phenylchromenylium cation). Anthocyanidins include: Aurantinidin, Cyanidin, Delphinidin, Europinidin, Luteolinidin, Pelargonidin, Malvidin, Peonidin, Petunidin, Rosinidin, andXanthone.

The antioxidant may be a Dihydrochalcone (derivative of 1,3-diphenyl-1-propanone). Dihydrochalcones include: Phloretin, Dihydrochalcone phloretin Phlorizin, Aspalathin, Naringin dihydrochalcone, Neohesperidin dihydrochalcone, and Nothofagin. Without limiting the mode of action of the invention, dihydrochalcones may exert an antioxidant effect by reducing reactive free radicals, like reactive oxygen and reactive nitrogen species.

The antioxidant may be an anthocyanin. Anthocyanins and their derivatives are antioxidants. Anthocyanins encompasses a class of flavonoid compounds that are naturally occurring, water-soluble compounds, responsible for the red, purple, and blue colors of many fruits, vegetables, cereal grains, and flowers. Additionally, anthocyanins are collagenase inhibitors. The inhibition of collagenase helps in the prevention and reduction of wrinkles, increase in skin elasticity, etc., which are caused by a reduction in skin collagen. The anthocyanins may be obtained from any portion of various plant sources, such as the fruit, flower, stem, leaves, root, bark, or seeds. One of skill in the art will understand that certain portions of the plant may contain higher natural levels of anthocyanins, and, therefore, those portions are used to obtain the desired anthocyanins. In some instances, antioxidants may include one or more betacyanin. Betacyanins, like anthocyanins, may be obtained from natural sources and are antioxidants.

The antioxidant may be a Phenylpropanoid (derivatives of cinnamic acid). Phenylpropanoids include: Cinnamic acid, Caffeicacid, Ferulicacid, Trans-ferulie acid (including its antioxidant pharmacore 2,6-dihydroxyacetophenome), 5-Hydroxyferulic acid, Sinapicacid, Coumaryl alcohol, Coniferyl alcohol, Sinapyl alcohol, Eugenol, Chavicol, Safrole, P-coumaric acid, and Sinapinic acid. Without limiting the mode of action of the invention, Phenylpropanoids may neutralize free radicals.

The antioxidant may be a Chalcone (derivative of 1,3-diphenyl-2-propen-1-one). Chalcones include: Butein, Okanin, Carthamin, Marein, Sophoradin, Xanthohumol, Flavokvain A, Flavokavain B, Flavokavin C, and synthetic Safalcone.

The antioxidant may be a Curcuminoid. Curcuminoids include: Curcumin, Desmethoxycurcumin, bis-Desmethoxycurcumin, Tetrahydrocurcumin, and Tetrahydrocurcuminoids. Curcumin and tetrahydrocurcuminoids may be derived from rhizomes of *Curcuma longa*. Tetrahydrocurcumin, a metabolite of curcumin, has been found to be a more potent antioxidant and more stable compared to curcumin.

The antioxidant may be a Tannin. Tannins include: Tannin, Terflavin B, Glucogallin, Dgallic acid, and Quercitannic acid.

The antioxidant may be a stilbenoid. Stilbenoids include: Resveratrol, Pterostilbene, and Piceatannol. Resveratrol may include, but is not limited to, 3,5,4'-trihydroxystilbene, 3,4,3',5'-tetrahydroxystilbene (piceatannol), 2,3',4,5'-tetrahydroxystilbene (oxyresveratrol), 4,4'-dihydroxystilbene, and alpha and beta glucoside, galactoside and mannoside derivatives thereof.

The antioxidant may be a Coumarin (derivatives of 2H-chromen-2-one). Coumarins include: 4-Hydroxycoumarin, Umbelliferone, Aesculetin, Herniarin, Auraptene, and Dicoumarol.

The antioxidant may be a Carotenoid. Carotenoids include: beta-Carotene, alpha-Carotene, gamma-Carotene, beta-Cryptoxanthin, Lycopene, Lutein, and Idebenone. Sesame (*Sesamum indicum*) or sesame lignan may also be added. Sesame and its lignans (the fibrous compounds associated with the sesame) act as antioxidants. Sesame seed lignans significantly enhance vitamin E activity.

The antioxidant may be: a Xanthone, Butylated Hydroxytoluene, 2,6-Di-tert-butylphenol, 2,4-Dimethyl-6-tert-butylphenol, Gallic acid, Eugenol, Uric acid, alpha-Lipoic acid, Ellagic acid, Chicoric acid, Chlorogenic acid, Rosmarinic acid, Salicylic acid, Acetylcysteine, S-Allyl cysteine, Barbigerone, Chebulagic acid, Edaravone, Ethoxyquin, Glutathione, Hydroxytyrosol, Idebenone, Melatonin, N-Acetylserotonin, Nordihydroguaiaretic acid, Oleocanthal, Oleuropein, Paradol, Piceatannol, Probucol, Propyl gallate, Protocatechuic acid, Pyritinol, Rutin, Secoisolariciresinol diglucoside, Sesamin, Sesamol, Silibinin, Silymarin, Theaflavin, Theaflavin digallate, Thmoquinone, Trolox, Tyrosol, Polyunsaturated fatty acids, and sulfur-based antioxidants such as Methionine or Lipoic acid.

Optional Components

In one or more embodiments, the skin tightening compositions described herein may contain one or more additional ingredients (additives and miscellaneous ingredients). Examples include, but are not limited to surfactants, emulsifiers, thickeners (such as polysaccharide-based thickeners), other polymers, proteins, hydrolyzed proteins, amino acids, fragrance, pH adjusters, and preservatives. Additional details regarding such additional ingredients follows below.

The skin tightening composition according to the disclosure can comprise any additional ingredients suitable for use in skin tightening compositions. Such ingredients may include, but are not limited to, cosmetically acceptable solvents, silicone compounds, rheology modifying agents such as acrylic polymers, cationic, nonionic, amphoteric or zwitterionic surfactants or mixtures thereof, anionic, cationic, nonionic, amphoteric or zwitterionic polymers or mixtures, humectants and moisturizing agents, fatty substances other than the claimed fatty substances, emulsifying agents other than fatty substances, fillers, structuring agents, propellants, shine agents, conditioning agents, antioxidants or reducing agents, penetrants, sequestrants, fragrances, buffers, dispersants, conditioning agents, for instance volatile or non-volatile, modified or unmodified silicones, ceramides, preserving agents, opacifiers, sunscreen agents, and antistatic agents. Acids, for example citric acid, can affect the pH of the system resulting in loss of lift.

The skin tightening composition may also contain acid and alkali pH adjusters, which are well known in the art. Such pH adjusters include, but are not limited to, sodium metasilicate, silicate compounds, citric acid, ascorbic acid, and carbonate compounds.

Methods

The skin tightening compositions are particularly useful for improving the appearance of skin, especially the skin of a human. When the skin tightening compositions are applied to the skin, they provide an immediate improvement to the appearance of the skin that is long lasting. The skin tightening compositions are particularly useful for method of:
- reducing the appearance of fine lines of the skin;
- reducing the appearance of wrinkles of the skin;
- improving the tone of skin and/or improving the evenness of skin tone;
- improving skin softness and/or smoothness;
- reducing the appearance of eye bags;
- reducing the appearance of dark circles around and/or below the eyes;
- reducing the appearance of pores and/or scars; and/or
- increasing the radiance, luminosity, and/or glow of the skin.

Typically, an effective amount of a skin tightening composition is applied to the skin to be treated, for example, the skin of the face and/or neck. In some instances, it may be desirable to apply the skin tightening composition to the skin around (or below) the eyes. The skin tightening compositions can be applied with the hands or may be applies using a brush, sponge, tissue, cotton swab, fabric, or applicator (e.g., pen or other device), etc. The amount needed to achieve the desired effect can be ascertained by the consumer.

EMBODIMENTS OF THE DISCLOSURE

In certain embodiments, skin tightening compositions according to the instant disclosure comprises or consists of:
 about 5 wt. % or more, preferably about 5 wt. % to about 30 wt. %, more preferably about 6 wt. % to about 25 wt. % of one or more hydrophobic film-forming polymers comprising acrylates/stearyl methacrylate copolymer;
 about 0.51 to about 20 wt. %, preferably about 1 to about 15 wt. %, more preferably about 1 to about 10 wt. % of one or more mineral thickening agents, preferably one or more optionally modified silicas and/or one or more optionally modified clays, in particular, hydrophobic silica aerogels (e.g., silica silylate) and/or organophilic modified clays (e.g., organophilic modified hectorites such as disteardimonium hectorite);

wherein a weight ratio of the total amount of hydrophobic film-forming polymers to the total amount of mineral thickening agent is 1:1 to 10:1, preferably 1:1 to 7:1, more preferably 1:1 to 6:1;

about 1 to about 15 wt. %, preferably about 1 to about 30 wt. %, more preferably about 5 to about 25 wt. % of one or more silicone elastomers, which may be emulsifying or non-emulsifying, in particular, at least one non-emulsifying silicone elastomer such as a a cross-linked silicone selected from dimethicone crosspolymer, (dimethicone/vinyl dimethicone) crosspolymer, (dimethicone/phenyl vinyl dimethicone) crosspolymer, (vinyl dimethicone/lauryl dimethicone) crosspolymer, (lauryl polydimethylsiloxyethyl dimethicone/bis-vinyl dimethicone) crosspolymer, alkyl (C30-45) cetearyl dimethicone crosspolymer, cetearyl dimethicone crosspolymer, and a mixture thereof; and about 30 to about 85 wt. %, preferably about 35 to about 80 wt. %, more preferably about 40 to about 75 wt. % of one or more volatile hydrocarbon oils, preferably, one or more volatile hydrocarbon oils are selected from branched $C_8$ to $C_{16}$ alkanes, such as, for example, isoparaffin, isohexadecane, isododecane, isodecane, undecane, tridecane, dodecane, and a mixture thereof, wherein a weight ratio of the total amount of silicone elastomer to the total amount of mineral thickening agent is 1:2 to 8:1, preferably about 1.1:1 to about 4:1, more preferably about 1.2:1 to about 4:1, and all percentages by weight are based on the total weight of the skin tightening composition.

In additional embodiments, skin tightening compositions according to the instant disclosure comprises or consists of:

about 5 to about 45 wt. %, preferably about 6 to about 40 wt. %, more preferably about 8 to about 35 wt. %, of one or more hydrophobic film-forming polymers comprising acrylates/stearyl methacrylate copolymer;

about 1 to about 35 wt. %, preferably about 4 to about 35 wt. %, more preferably about 6 to about 25 wt. %, of a thickening agent selected from polyamide-8, styrene ethylene/propylene copolymer, and nylon-611/dimethicone crosspolymer, VP/EICOSENE Copolymer, fumed silica, hydrophobically modified silica, silica silylate, clays or a combination thereof, wherein a weight ratio of the total amount of hydrophobic film-forming polymers to the total amount of thickening agent is 1:2 to 10:1, preferably, 1:2 to 7:1, more preferably 1:2 to 6:1;

about 0.5 to about 20 wt. %, preferably about 2 to about 11 wt. %, more preferably about 2.5 to about 9 wt. % of a filler, such as those chosen from silica sylilate, silica, nylon-12, cellulose, methyl methacrylate crosspolymer, and polymethylsilsesquioxane, and a combination thereof;

about 20 to about 85 wt. %, preferably about 25 to about 85 wt. %, more preferably about 25 to about 80 wt. %, of a volatile hydrocarbon, the volatile hydrocarbon optionally be chosen from isoparaffin, isohexadecane, isododecane, isodecane, undecane, tridecane, dodecane, isohexyl, isodecyl, neopentanoate, or a combination thereof, wherein all weight percentages are based on the total weight of the skin tightening composition.

EXAMPLES

Implementation of the present disclosure is provided by way of the following examples. The following examples serve to elucidate aspects of the technology without being limiting in nature.

Example 1

An exemplary skin tightening composition (Exemplary Composition 1) and a comparative skin tightening composition (Comparative Composition A) were prepared in accordance with the formulations provided in Table 1. Exemplary Composition 1 and Comparative Composition A were assessed to determine the sebum resistance, odor profile, gloss, transparency, haze, and skin tightening effect of such compositions.

The sebum resistance was assessed by evaluating the films formed from Exemplary Composition 1 and Comparative Composition A. Specifically, using a draw down bar at 8 mil (200 um), a sample of Exemplary Composition 1 and Comparative Composition A were spread on a black contrast card (BYK). The samples were allowed to dry on the substrate for a minimum of 3 hours. A drop of artificial sebum was deposited and left on the films formed from each of Exemplary Composition 1 and Comparative Composition A for 3 hours and, then absorbed with absorbing paper. The area was then rubbed 15 times with a cotton swab.

Film quality was then ranked as follows: all film area exposed to artificial drop is removed by cotton swab rubbing, which is associated with no sebum resistance; "+" more than 50% of film area exposed to the artificial drop is removed by cotton swab rubbing, which corresponds to mild sebum resistance; "++" less than 50% of film area exposed to artificial drop was removed by cotton swab rubbing, which corresponding to good sebum resistance; "+++" none of the film area exposed to artificial drop was removed by cotton swab rubbing, which is associated with strong sebum resistance.

Exemplary Composition 1 and Comparative Composition A were also assessed to determine the gloss, transparency, and haze of films formed from such compositions. Specifically, films were formed from Exemplary Composition 1 and Comparative Composition A using a draw down bar at 8 mil (200 um) to spread the compositions on a transparent plastic substrate. The samples of Exemplary Composition 1 and Comparative Composition A were allowed to dry on the transparent plastic substrate for 3 hours. A BYK Haze-Guard instrument was used to measure the transparency and the haze for the films of Exemplary Composition 1 and Comparative Composition A. A BYK Glossmeter was used to measure the gloss and mattness, against a black contrast card at an angle of 60°.

The skin tightening effects of Exemplary Composition 1 and Comparative Composition were evaluated by applying each of the compositions to a volunteer. A "+++" was given to compositions that provide significant skin tightening effect.

Exemplary Composition 1 and Comparative Composition A were qualitatively assessed to determine their odor profile. The results of the evaluation of the the sebum resistance, odor profile, gloss, transparency, haze, and skin tightening effect of Exemplary Composition 1 and Comparative Composition A are provided in Table 1, below.

TABLE 1

| | INCI US | Ex. 1 | Comp. A |
|---|---|---|---|
| Volatile Hydrocarbon Oil | ISODODECANE | 78.15 | 78.15 |
| Silicone Elastomer | DIMETHICONE CROSSPOLYMER | 5.78 | 5.78 |
| Mineral Thickening Agent | SILICA SILYLATE | 3.86 | 3.86 |
| Weight ratio of silicone elastomer to mineral thickening agent | | 1.50 | 1.50 |
| Hydrophobic Film-Forming Polymer | ACRYLATES/STEARYL METHACRYLATE COPOLYMER | 12.21 | |
| | ACRYLATES/ISOBORNYL ACRYLATE COPOLYMER | | 12.21 |
| Weight ratio of hydrophobic film-forming polymer to mineral thickening agent | | 3.16 | 3.16 |
| TOTAL | | Q.S. to 100 | Q.S. to 100 |

TABLE 1-continued

| | INCI US | Ex. 1 | Comp. A |
|---|---|---|---|
| | Transparency | 95.3 | 95.1 |
| | Haze | 95.3 | 94.4 |
| | Gloss at 60 | 7.5 | 9.8 |
| | Smell | + | ++ |
| | In vitro sebum resistance | +++ | − |
| | Under eye wrinkles and bags reduction | +++ | +++ |

After assessing the odor profile of Exemplary Composition 1 and Comparative Composition A, it was determined that Exemplary Composition 1 exhibited a more natural odor and Comparative Composition A exhibited a more chemical odor. Exemplary Composition 1 exhibited a surprising amount of sebum resistance, especially in view of the similarity in formulation to Comparative Composition A.

Example 2

Two exemplary skin tightening compositions (Exemplary Compositions 2 and 3) and two comparative skin tightening compositions (Comparative Compositions B and C) were prepared according to the formulations provided in Table 2. Exemplary Compositions 2 and 3 and Comparative Compositions B and C were assessed to determine the sebum resistance, gloss, transparency, haze, and skin tightening effect of such compositions using evaluation techniques discussed in Example 1.

TABLE 2

| | INCI US | Ex. 2 | Ex. 3 | Comp. B | Comp. C |
|---|---|---|---|---|---|
| Volatile Hydrocarbon Oil | ISOPARAFFIN | 39.59 | 31.67 | 39.59 | 31.67 |
| | ISODODECANE | 38.56 | 30.84 | 38.56 | 30.84 |
| Silicone Elastomer | DIMETHICONE CROSSPOLYMER | 5.78 | 4.63 | 5.78 | 4.63 |
| Mineral Thickening Agent | SILICA SILYLATE | 3.86 | 3.09 | 3.86 | 3.09 |
| Weight ratio of silicone elastomer to mineral thickening agent | | 1.50 | 1.50 | 1.50 | 1.50 |
| Hydrophobic Film-Forming Polymer | ACRYLATES/STEARYL METHACRYLATE COPOLYMER | 12.21 | 9.77 | | |
| | ACRYLATES/ISOBORNYL ACRYLATE COPOLYMER | | | 12.21 | 9.77 |
| Weight ratio of hydrophobic film-forming polymer to mineral thickening agent | | 3.16 | 3.16 | 3.16 | 3.16 |
| Surfactant | LAURYL PEG-9 POLYDIMETHYLSILOXYETHYL DIMETHICONE | | 1.5 | | 1.5 |
| | DIMETHICONE (and) PEG/PPG-18/18 DIMETHICONE | | 2 | | 2 |
| Solvent | WATER | | 15.45 | | 15.45 |
| Salt | MAGNESIUM SULFATE | | 0.25 | | 0.25 |
| Preservative | PHENOXYETHANOL | | 0.5 | | 0.5 |
| | CAPRYLYL GLYCOL | | 0.3 | | 0.3 |
| TOTAL | | Q.S. to 100 | Q.S. to 100 | Q.S. to 100 | Q.S. to 100 |
| Transparency | | 95.2 | 94.6 | 94.9 | 93.7 |
| Haze | | 94.9 | 92.8 | 94.5 | 92.9 |
| Gloss at 60 | | 7.9 | 10.2 | 9.5 | 8.9 |
| Sebum resistance (in vitro) | | ++ | +++ | + | − |
| Under eye wrinkles and bags reduction | | +++ | +++ | +++ | +++ |

As seen in Table 2, Exemplary Compositions 2 and 3 exhibited better sebum resistance than Comparative Compositions B and C.

Example 3

Seven exemplary compositions (Exemplary Compositions 4-10) were prepared in accordance with aspects of the disclosure. The formulations for Exemplary Compositions 4-10 are provided below. Exemplary Compositions 4-10 were assessed to determine the gloss, transparency, and haze, of such compositions using evaluation techniques discussed in Example 1.

TABLE 3

| | INCI US | Ex. 4 | Ex. 5 | Ex. 6 | Ex. 7 | Ex. 8 | Ex. 9 | Ex. 10 | Ex. 11 |
|---|---|---|---|---|---|---|---|---|---|
| Volatile Hydrocarbon Oil | ISOPARAFFIN | 2.26 | 24.08 | | | | | | |
| | ISODODECANE | 57.22 | 53.21 | 59.07 | 76.15 | 60.51 | 80.00 | 76.60 | 55.51 |
| Silicone Elastomer | DIMETHICONE CROSSPOLYMER | 5.78 | 9.00 | 6.19 | 5.78 | 4.63 | 6.25 | 14.40 | 4.63 |
| Mineral Thickening Agent | SILICA SILYLATE | 3.86 | 1.5 | 3.86 | 3.86 | 3.09 | 1.25 | 1.8 | 3.09 |
| | Weight ratio of silicone elastomer to mineral thickening agent | 1.50 | 6.00 | 1.60 | 1.50 | 1.50 | 5.00 | 8.00 | 1.50 |
| Hydrophobic Film-Forming Polymer | ACRYLATES/STEARYL METHACRYLATE COPOLYMER | 30.88 | 12.21 | 30.88 | 12.21 | 9.77 | 12.50 | 7.20 | 9.77 |
| | Weight ratio of hydrophobic film-forming polymer to mineral thickening agent | 8.00 | 8.14 | 8.00 | 3.16 | 3.16 | 10.00 | 4.00 | 3.16 |
| Surfactants | LAURYL PEG-9 POLYDIMETHYLSILOXYETHYL DIMETHICONE | | | | | 1.5 | | | 1.5 |
| | DIMETHICONE (and) PEG/PPG-18/18 DIMETHICONE | | | | | 2 | | | 2 |
| Dispersing Agent | POLYHYDROXYSTEARIC ACID | | | | 2 | 2 | | | 2 |
| Solvent | WATER | | | | | 15.45 | | | 15.45 |
| Salt | MAGNESIUM SULFATE | | | | | 0.25 | | | 0.25 |
| Preservative | PHENOXYETHANOL | | | | | 0.5 | | | 0.5 |
| | CAPRYLYL GLYCOL | | | | | 0.3 | | | 0.3 |
| Pigments | ALUMINA (and) IRON OXIDES (and) TITANIUM DIOXIDE (and) TRIETHOXYCAPRYLYLSILANE (and) SILICA DIMETHYL SILYLATE (and) TALC (and) POLYHYDROXYSTEARIC ACID | | | | | | | | 5 |
| | TOTAL | Q.S. to 100 | Q.S. to 100 | Q.S. to 100 | Q.S. to 100 | Q.S. to 100 | Q.S. to 100 | Q.S. to 100 | Q.S. to 100 |
| | Transparency | 96.1 | 95.3 | 93.5 | 94.9 | 94.2 | 94.5 | 94.9 | 34.3 |
| | Haze | 96.8 | 94.8 | 96.9 | 95.2 | 94.4 | 94.5 | 94.4 | 99.8 |
| | Gloss at 60 | 6.2 | 7.8 | 4.9 | 7.5 | 8.5 | 8.7 | 7.9 | 1.8 |

Example 4

Five exemplary compositions (Exemplary Compositions 12-15) were prepared in accordance with aspects of the disclosure. The formulations for Exemplary Compositions 12-15 are provided below. Exemplary Compositions 12-15 were assessed to determine the gloss, transparency, and haze of such compositions using evaluation techniques discussed in Example 1.

TABLE 4

| | INCI US | Ex. 12 | Ex. 13 | Ex. 14 | Ex. 15 |
|---|---|---|---|---|---|
| Volatile Hydrocarbon Solvents | ISODODECANE | 63.75 | 40.97 | 38.3 | 40.97 |
| | ISOPARAFFIN | | 37.15 | 33.58 | 37.15 |
| Optical Fillers | SILICA SILYLATE | | | 3.13 | 3.13 |
| | NYLON-12 | | 3.13 | | |
| | POLYMETHYLSILSESQUIOXANE | 15 | | | |
| Organic Thickeners | DIMETHICONE CROSSPOLYMER | 6.25 | 6.25 | | |
| | POLYAMIDE-8 | | | 12.5 | |
| | HYDROGENATED STYRENE/ISOPRENE COPOLYMER | | | | 6.25 |
| Film Forming Polymer | ACRYLATES/STEARYL METHACRYLATE COPOLYMER | 15 | 12.5 | 12.5 | 12.5 |
| | Weight ratio of film forming polymer to organic thickener | 2.4 | 2 | 1 | 2 |
| | TOTAL | Q.S. to 100 | Q.S. to 100 | Q.S. to 100 | Q.S. to 100 |
| | Transparency | 94.8 | 91.0 | 95.9 | 92.9 |
| | Haze | 98.9 | 95.5 | 94.6 | 83.9 |
| | Gloss at 60° | 3.7 | 5.5 | 14.3 | 7.9 |

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

The term "INCI" is an abbreviation of International Nomenclature of Cosmetic Ingredients, which is a system of names provided by the International Nomenclature Committee of the Personal Care Products Council to describe personal care ingredients.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

All components and elements positively set forth in this disclosure can be negatively excluded from the claims. In other words, the skin tightening compositions of the instant disclosure can be free or essentially free of all components and elements positively recited throughout the instant disclosure.

Some of the various categories of components identified may overlap. In such cases where overlap may exist and the composition includes both components (or the composition includes more than two components that overlap), an overlapping compound does not represent more than one component. For example, a fatty acid may be characterized as both a nonionic surfactant and a fatty compound. If a particular composition includes both a nonionic surfactant and a fatty compound, a single fatty acid will serve as only the nonionic surfactant or as only the fatty compound (the single fatty acid does not serve as both the nonionic surfactant and the fatty compound).

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

As used herein, the terms "comprising," "having," and "including" are used in their open, non-limiting sense.

The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

The expression "one or more" means "at least one" and thus includes individual components as well as mixtures/combinations.

Other than in the operating examples, or where otherwise indicated, all numbers expressing quantities of ingredients and/or reaction conditions may be modified in all instances by the term "about," meaning within +/−5% of the indicated number.

The term "treat" (and its grammatical variations) as used herein refers to the application of the compositions of the present disclosure onto the surface of keratinous substrates such as skin, in particular, the skin of the head, face, and neck.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. All of the components set forth herein may be optionally included or excluded from the compositions/method/kits. When excluded, the compositions/methods/kits may be free or essentially free of the component. For example, a particular composition may be free or essentially free of alkoxylated compounds, for example, ethoxylated thickening agents and/or ethoxylated surfactants. Likewise, a particular composition may be free or essentially free of sulfates, such as sulfate surfactants.

What is claimed is:

1. A skin tightening composition comprising:
   about 5 to about 45 wt. % or more of one or more hydrophobic film-forming polymers comprising acrylates/stearyl methacrylate copolymer;
   about 0.5 to about 20 wt. % of a mineral thickening agent, wherein a weight ratio of the total amount of hydrophobic film-forming polymers to the total amount of mineral thickening agent is 1:1 to 10:1;
   about 1 to about 15 wt. % of a silicone elastomer; and
   about 30 to about 85 wt. % of a volatile hydrocarbon oil, wherein a weight ratio of the total amount of silicone elastomer to the total amount of mineral thickening agent is 1:2 to 8:1, and all percentages by weight are based on the total weight of the skin tightening composition.

2. The skin tightening composition of claim 1, wherein the mineral thickening agent is chosen from silica silylate, fumed silica, zeolite, natural clay, synthetic clay, kaolin, hectorite, organically modified hectorite, pentaerythrityl tetraisostearate (and) disteardimonium hectorite (and) propylene carbonate, an activated clay, disteardimonium hectorite, stearalkonium hectorite, quaternium-18 bentonite, quaternium-18 hectorite, benzalkonium bentonite, and a mixture thereof.

3. The skin tightening composition of claim 1, wherein the silicone elastomer is chosen from non-emulsifying silicone elastomers, emulsifying silicone elastomers, and a mixture thereof.

4. The skin tightening composition of claim 1, wherein the weight ratio of the total amount of silicone elastomer to the total amount of mineral thickening agent is 1:1 to 7:1.

5. The skin tightening composition of claim 1, wherein a weight ratio of the total amount of hydrophobic film-forming polymers to the total amount of mineral thickening agent is 1:1 to 8:1.

6. The skin tightening composition of claim 1, further comprising:
about 0.1 to about 20 wt. % of a non-volatile fatty compound, wherein the one or more non-volatile fatty compounds are chosen from polyolefins (petrolatum), waxes, squalane, squalene, hydrogenated polyisobutene, hydrogenated polydecene, polybutene, mineral oil, pentahydrosqualene, dimethicone, and a mixture thereof.

7. The skin tightening composition of claim 1, further comprising:
about 0.01 to about 20 wt. % of an inorganic pigment, wherein the inorganic pigment is chosen from titanium dioxide, mica, zirconium oxide, cerium oxide, zinc oxide, iron oxide, alumina, aluminum hydroxide, chromium oxide, manganese violet, ultramarine blue, chromium hydrate, ferric blue, aluminum powder, copper powder, silver powder, gold powder, barium sulfate, carbon black, and a mixture thereof.

8. The skin tightening composition of claim 1, further comprising:
about 0.1 to about 20 wt. % of soft focus powder, wherein the soft focus powder is chosen from talc, mica, cellulose, nylon-12, titanated mica, alumina, aluminum silicate, silica which may or may not be coated, fumed silica, polyamide, methyl methacrylate crosspolymer, poly(methyl (meth)acrylate), polyethylene powder, polymethylsilsesquioxane powder, nylon-12 fluorescent brightener salt (and) polyvinylalcohol crosspolymer, and a mixture thereof.

9. The skin tightening composition of claim 1 further comprising:
about 0.1 to 10 wt. % of a dispersant.

10. A method for improving the appearance of skin comprising applying a skin tightening composition of claim 1 to the skin.

11. The method of claim 10, wherein the method of improving the appearance of skin comprises:
reducing the appearance of fine lines of the skin;
reducing the appearance of wrinkles of the skin;
improving the tone of skin and/or improving the evenness of skin tone;
improving skin softness and/or smoothness;
reducing the appearance of eye bags;
reducing the appearance of dark circles around and/or below the eyes;
reducing the appearance of pores and/or scars; and/or
increasing the radiance, luminosity, and/or glow of the skin.

12. A skin tightening composition comprising:
about 5 to about 45 wt. % of one or more hydrophobic film-forming polymers comprising acrylates/stearyl methacrylate copolymer;
about 1 to about 35 wt. % of a thickener chosen from polyamide-8, hydrogenated styrene/isoprene copolymer, nylon-611/dimethicone copolymer, dimethicone/vinyl dimethicone crosspolymer, dimethicone crosspolymer, VP/EICOSENE copolymer, fumed silicas, hydrophobically modified silica, silica silylate, clays, and a combination thereof,
wherein a weight ratio of the total amount of hydrophobic film-forming polymers to the total amount of thickener is 1:2 to 10:1;
about 0.5 to about 20 wt. % of a filler; and
about 20 to about 85 wt. % of a volatile hydrocarbon,
wherein and all weight percentages are based on the total weight of the skin tightening composition.

13. The skin tightening composition of claim 12, wherein the filler is chosen from a silica silylate, nylon-12, cellulose, methacrylate crosspolymer, silicone powder, and a mixture thereof.

14. The skin tightening composition of claim 13, wherein the filler comprises a hydrophobic silica.

15. The skin tightening composition of claim 14, wherein the hydrophobic silica is silica silylate.

16. The skin tightening composition of claim 12, wherein the volatile hydrocarbon is chosen from isoparaffin, isohexadecane, isododecane, isodecane, undecane, tridecane, dodecane, isohexyl, isodecyl, neopentanoate, and a mixture thereof.

17. The skin tightening composition of claim 12, further comprising:
about 1 to about 10 wt. % of a non-ionic surfactant, wherein the non-ionic surfactant is chosen from dimethicone (and) peg/ppg-18/18 dimethicone, lauryl peg-9 polydimethylsiloxyethyl dimethicone, cetyl peg/ppg-10/1 dimethicone, peg-30 dipolyhydroxystearate, polyglyceryl-4 diisostearate/polyhydroxystearate/sebacate, polyglyceryl-4 isostearate, polyglyceryl-2 dipolyhydroxystearate, and a mixture thereof.

18. The skin tightening composition of claim 12, further comprising:
about 1 to about 10 wt. % of a dispersant, wherein the dispersant is chosen from olyoxyethylene glycol ethers, POE/PEG ethers or esters, polyoxypropylene glycol ethers, PPG ethers or esters, sugar ethers or esters, glycerol or polyglycerol ethers or esters, and from ethoxylated glyceride esters, polyhydroxystearic acid, and a mixture thereof.

19. The skin tightening composition of claim 12, further comprising:
about 0.01 to about 20 wt. % of an inorganic pigment, wherein the inorganic pigment is chosen from titanium dioxide, zirconium oxide, cerium oxide, zinc oxide, iron oxide, mica, alumina, aluminum hydroxide, chromium oxide, manganese violet, ultramarine blue, chromium hydrate, ferric blue, aluminum powder, copper powder, silver powder, gold powder, barium sulfate, carbon black, and a mixture thereof.

20. The skin tightening compositions of claim 12, wherein the weight ratio of the total amount of hydrophobic film-forming polymers to the total amount of thickener is 1:2 to 8:1.

* * * * *